United States Patent
Rajopadhye

(10) Patent No.: US 6,818,659 B2
(45) Date of Patent: Nov. 16, 2004

(54) (2S)-2-AMINO-4-(2-AMINO-(3,4,5, 6-TETRAHYDROPYRIMIDIN-4-YL) BUTANOYL AND ITS USE IN CYCLIC AND ACYCLIC PEPTIDES

(75) Inventor: Milind Rajopadhye, Westford, MA (US)

(73) Assignee: Bristol-Myers Squibb Pharma, Inc., Princeton, NJ (US)

( * ) Notice: Subject to any disclaimer, the term of this patent is extended or adjusted under 35 U.S.C. 154(b) by 200 days.

(21) Appl. No.: 10/008,180

(22) Filed: Nov. 6, 2001

(65) Prior Publication Data

US 2004/0087603 A1 May 6, 2004

(51) Int. Cl.[7] .......................... C07D 239/02; C07K 7/00; C07K 16/00
(52) U.S. Cl. ..................... 514/330; 514/332; 530/300; 530/333
(58) Field of Search ................ 544/330, 332; 530/300, 333

(56) References Cited

U.S. PATENT DOCUMENTS

| | | | |
|---|---|---|---|
| 4,973,592 A | * 11/1990 | Nicola et al. | 514/269 |
| 5,332,745 A | 7/1994 | Carter et al. | 514/275 |
| 5,854,234 A | 12/1998 | Hansen, Jr. et al. | 514/212 |

FOREIGN PATENT DOCUMENTS

| | | |
|---|---|---|
| JP | 63/227573 | 9/1988 |
| WO | WO 9505381 | 2/1995 |
| WO | WO 0061545 | 10/2000 |

OTHER PUBLICATIONS

Duggan et al, J. Med. Chem. 2000, 43, 3736–3745.
Adlington, RM et al., 1999, J. Chem. Soc., Perkin Trans. 1, 8, 855–866.
Gopalsamy et al. Bioorg. Med. Chem. Lett. 2000, 10(15), 1715–1718.

* cited by examiner

*Primary Examiner*—Richard L. Raymond
*Assistant Examiner*—Tamthom N. Truong
(74) *Attorney, Agent, or Firm*—Stephen B. Davis, Esq.; Woodcock Washburn LLP

(57) ABSTRACT

The present invention provides a novel amino acid of the formula:

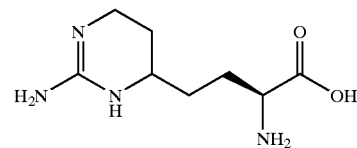

and derivatives thereof that are useful as arginine substitutes in biological targeting moieties.

15 Claims, No Drawings

(2S)-2-AMINO-4-(2-AMINO-(3,4,5,6-TETRAHYDROPYRIMIDIN-4-YL) BUTANOYL AND ITS USE IN CYCLIC AND ACYCLIC PEPTIDES

FIELD OF THE INVENTION

The present invention provides a novel arginine mimic, (2S)-2-amino-4-(2-amino-(3,4,5,6-tetrahydropyrimidin-4-yl))butanoyl, methods of using the same, peptides that bind to biological receptors containing the same, and pharmaceuticals comprising the same.

The pharmaceuticals are comprised of a targeting moiety that binds to a biological receptor, an optional linking group, and a therapeutically effective radioisotope or diagnostically effective imageable moiety. The therapeutically effective radioisotope emits a particle or electron sufficient to be cytotoxic. The imageable moiety is a gamma ray or positron emitting radioisotope, a magnetic resonance imaging contrast agent, an X-ray contrast agent, or an ultrasound contrast agent.

BACKGROUND OF THE INVENTION

JP 07/030037 describes antithrombotics of the following formula.

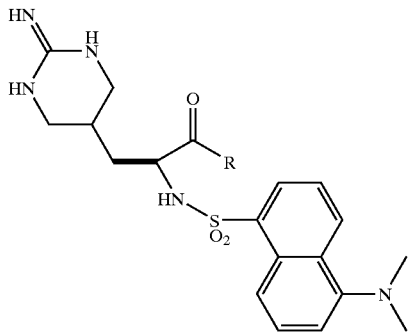

Compounds of this sort are not considered to be part of the present invention.

U.S. Pat. No. 5,332,745 illustrates tetrahydropyrimidine fungicides of the following formula.

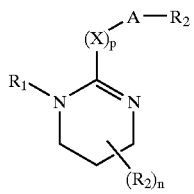

These types of compounds are not considered to be part of the present invention.

U.S. Pat. No. 5,854,234 depicts cyclic amidino nitric oxide synthase inhibitors of the following formula.

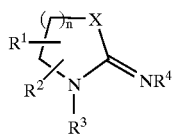

Such compounds are not considered to be part of the present convention.

Duggan et al, J. Med. Chem. 2000, 43, 3736–3745, describe non-peptide, $a_v b_3$ antagonists, an example of which is the following.

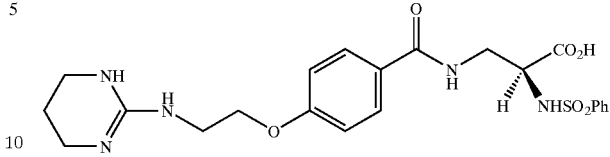

Such compounds are not considered to be part of the present invention.

SUMMARY OF THE INVENTION

It is one object of the present invention to provide a novel amino acid.

It is another object of the present invention to provide a novel method of making a novel amino acid.

It is another object of the present invention to provide a novel method of using a novel amino acid.

It is another object of the present invention to provide novel acyclic and cyclic peptides comprising a novel amino acid, wherein the peptides bind to a novel biological receptor.

It is another object of the present invention to provide novel pharmaceuticals comprising a targeting moiety that binds to a biological receptor, an optional linking group, and a therapeutically effective radioisotope or diagnostically effective imageable moiety, wherein the targeting moiety is an acyclic or cyclic peptide comprising a novel amino acid.

These and other objects, which will become apparent during the following detailed description, have been achieved by the inventors' discovery that the amino acid of formula I:

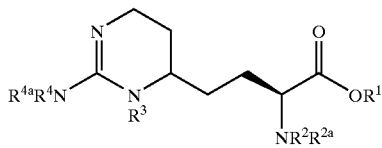

is an effective arginine mimic.

DETAILED DESCRIPTION OF THE INVENTION

Thus, in an embodiment, the present invention provides a novel compound of formula I:

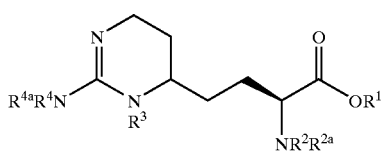

or a stereoisomer or salt form thereof, wherein:
$R^1$ is H or a hydroxy protecting group;
alternatively, $OR^1$ is an activated ester;
$R^2$ is H, $CH_3$, or an amine protecting group;
$R^{2a}$ is H or an amine protecting group;
$R^3$ is H or an amine protecting group;

R⁴ is H or an amine protecting group; and,
R⁴ᵃ is H or an amine protecting group;
provided that one of $R^1$, $R^2$, $R^{2a}$, $R^3$, $R^4$, and $R^4$ is other than H.

In another embodiment, the present invention provides a novel compound of formula Ia or Ib:

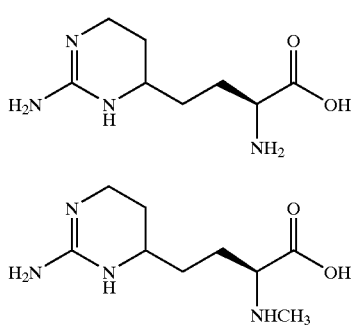

or a stereoisomer or salt form thereof.

In another preferred embodiment, the present invention provides a compound of formula I, wherein:
 $R^1$ is selected from H, OMe, OEt, OBzl, Oallyl, and Ot-Bu;
 alternatively, $OR^1$ is selected from OSu, OBt, OPfp, and Onp;
 $R^2$ is Fmoc or Boc
 $R^{2a}$ is H;
 $R^3$ is H;
 $R^4$ is selected from Tos, Mtr, Pbf, Mts, Pmc, Boc, Mbs, $NO_2$, and Cbz;
 $R^{4a}$ is H;
 alternatively, when $R^4$ Boc, $R^4$ is Boc; and,
 alternatively, when $R^4$ Cbz, $R^{4a}$ is Cbz;

In a more preferred embodiment, the compound of I is selected from:
 Fmoc-cyArg(Tos)-OH, Fmoc-cyArg(Mtr)-OH, Fmoc-cyArg(Pbf)-OH, Fmoc-cyArg(Mts)-OH, Fmoc-cyArg(Pmc)-OH, Fmoc-cyArg(Boc)2-OH, Boc-cyArg(Mbs)-OH, Boc-cyArg(Boc)2-OH, Boc-cyArg(Mtr)-OH, Boc-cyArg(NO₂)-OH, Boc-cyArg(Pbf)-OH, Boc-cyArg(Pmc)-OH, Boc-cyArg(Tos)-OH, and Boc-cyArg(Cbz)2-OH;
 wherein cyArg corresponds to the unmodified amino acid.

In another embodiment, the present invention provides a novel process for making a compound of formula I:

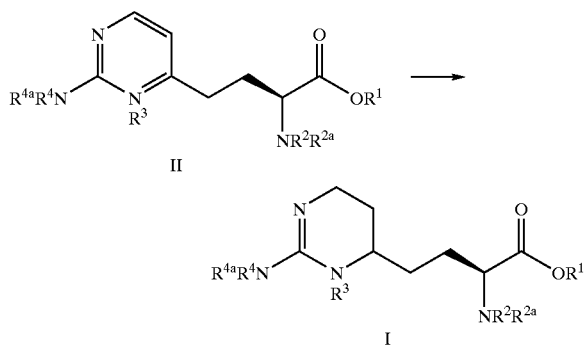

the process comprising: reducing a pyrimidine of formula II to form a compound of formula I.

In a preferred embodiment, reduction is performed by contacting the compound of formula II with trifluoroacetic acid and a trialkylsilane. One of ordinary skill in the art would recognize that a number of trialkylsilanes could be used for this reduction, including trimethylsilane, triethylsilane, and triisopropylsilane. Alternatively, the reduction is performed via catalytic hydrogenation.

In a more preferred embodiment, the trialkylsilane is triisopropylsilane.

A method of preparing an arginine-containing peptide, comprising: synthesizing the peptide using a compound of formula I in place of arginine or protected arginine:

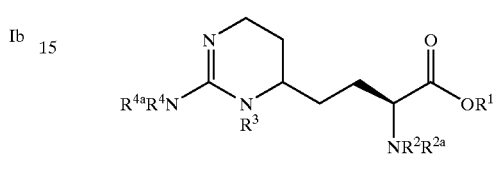

or a stereoisomer or salt form thereof, wherein:
 $R^1$ is H or a hydroxy protecting group;
 alternatively, $OR^1$ is an activated ester;
 $R^2$ is H or an amine protecting group;
 $R^{2a}$ is H or an amine protecting group;
 $R^3$ is H or an amine protecting group;
 $R^4$ is H or an amine protecting group; and,
 $R^{4a}$ is H or an amine protecting group;
 provided that one of $R^1$, $R^2$, $R^{2a}$, $R^3$, $R^4$, and $R^4$ is other than H.

In another embodiment, the present invention provides a novel compound, comprising: an acyclic or cyclic peptide that targets a biological receptor, wherein the peptide comprises an arginine mimic of formula IIIa or IIIb:

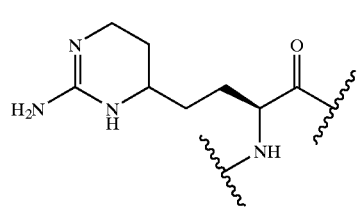

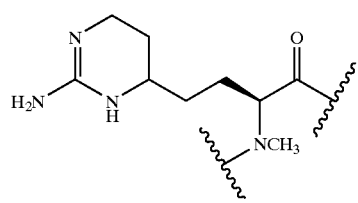

In another preferred embodiment, the biological receptor is selected from the group: Tuftsin, Thrombin catalytic site, Thrombin exosite, Factor XIIIa, Factor Xa, Factor IXa, Factor VIIa, Neurotensin, Bombesin, the Bradykinin receptors, and an intergrin selected $a_vb_3$, $a_{IIb}b_3$, $a_vb_5$, $a_5b_1$, $a_2b_1$, $a_1b_1$, and Mac-1

In a more preferred embodiment, the biological receptor is selected from the group: Tuftsin, Thrombin catalytic site, Thrombin exosite, Factor XIIIa, Factor Xa, Factor IXa, Factor VIIa, and an intergrin selected from $a_vb_3$, $a_{IIb}b_3$, $a_vb_5$, $a_5b_1$, $a_2b_1$, $a_1b_1$, and Mac-1

In another more preferred embodiment, the peptide comprises an RGD, TKPR, or TKPPR segment wherein arginine has been replaced by the arginine mimic of formula III.

In an even more preferred embodiment, the compound further comprises: a chelator and 0–1 linking groups between the peptide and the chelator.

In a still more preferred embodiment, the linking group is present.

In another embodiment, the present invention provides a novel compound, comprising: a cyclic peptide that targets a biological receptor, a chelator, and a linking group between the chelator and peptide, wherein the receptor is the integrin $\alpha_v\beta_3$ and the compound is of the formula:

$(Q)_d-L_n-C_h$ or $(Q)_d-L_n-(C_h)_d$, wherein, Q is a peptide independently selected from the group:

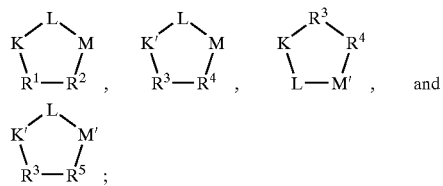

K is a group of formula IIIa or IIIb:

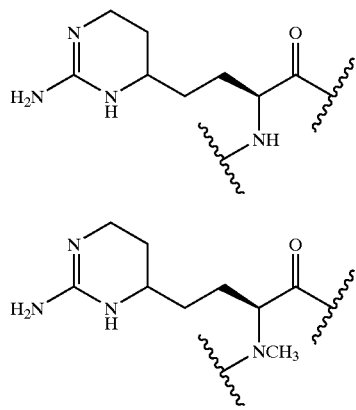

K' is a group of formula IIIc or IIIc:

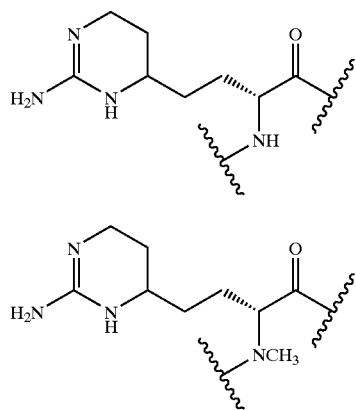

L is independently selected at each occurrence from the group: glycine, L-alanine, and D-alanine;

M is L-aspartic acid;

M' is D-aspartic acid;

$R^1$ is an amino acid substituted with 0–1 bonds to $L_n$, independently selected at each occurrence from the group: glycine, L-valine, D-valine, alanine, leucine, isoleucine, norleucine, 2-aminobutyric acid, 2-aminohexanoic acid, tyrosine, phenylalanine, thienylalanine, phenylglycine, cyclohexylalanine, homophenylalanine, 1-naphthylalanine, lysine, serine, ornithine, 1,2-diaminobutyric acid, 1,2-diaminopropionic acid, cysteine, penicillamine, and methionine;

$R^2$ is an amino acid, substituted with 0–1 bonds to $L_n$, independently selected at each occurrence from the group: glycine, valine, alanine, leucine, isoleucine, norleucine, 2-aminobutyric acid, 2-aminohexanoic acid, tyrosine, L-phenylalanine, D-phenylalanine, thienylalanine, phenylglycine, biphenylglycine, cyclohexylalanine, homophenylalanine, L-1-naphthylalanine, D-1-naphthylalanine, lysine, serine, ornithine, 1,2-diaminobutyric acid, 1,2-diaminopropionic acid, cysteine, penicillamine, methionine, and 2-aminothiazole-4-acetic acid;

$R^3$ is an amino acid, substituted with 0–1 bonds to $L_n$, independently selected at each occurrence from the group: glycine, D-valine, D-alanine, D-leucine, D-isoleucine, D-norleucine, D-2-aminobutyric acid, D-2-aminohexanoic acid, D-tyrosine, D-phenylalanine, D-thienylalanine, D-phenylglycine, D-cyclohexylalanine, D-homophenylalanine, D-1-naphthylalanine, D-lysine, D-serine, D-ornithine, D-1, 2-diaminobutyric acid, D-1,2-diaminopropionic acid, D-cysteine, D-penicillamine, and D-methionine;

$R^4$ is an amino acid, substituted with 0–1 bonds to $L_n$, independently selected at each occurrence from the group: glycine, D-valine, D-alanine, D-leucine, D-isoleucine, D-norleucine, D-2-aminobutyric acid, D-2-aminohexanoic acid, D-tyrosine, D-phenylalanine, D-thienylalanine, D-phenylglycine, D-cyclohexylalanine, D-homophenylalanine, D-1-naphthylalanine, D-lysine, D-serine, D-ornithine, D-1, 2-diaminobutyric acid, D-1,2-diaminopropionic acid, D-cysteine, D-penicillamine, D-methionine, and 2-aminothiazole-4-acetic acid;

$R^5$ is an amino acid, substituted with 0–1 bonds to $L_n$, independently selected at each occurrence from the group: glycine, L-valine, L-alanine, L-leucine, L-isoleucine, L-norleucine, L-2-aminobutyric acid, L-2-aminohexanoic acid, L-tyrosine, L-phenylalanine, L-thienylalanine, L-phenylglycine, L-cyclohexylalanine, L-homophenylalanine, L-1-naphthylalanine, L-lysine, L-serine, L-ornithine, L-1, 2-diaminobutyric acid, L-1,2-diaminopropionic acid, L-cysteine, L-penicillamine, L-methionine, and 2-aminothiazole-4-acetic acid;

provided that one of $R^1$, $R^2$, $R^3$, $R^4$, and $R^5$ in each Q is substituted with a bond to $L_n$, further provided that when $R^2$ is 2-aminothiazole-4-acetic acid, K is N-methylarginine, further provided that when $R^4$ is 2-aminothiazole-4-acetic acid, K and K' are N-methylarginine, and still further provided that when $R^5$ is 2-aminothiazole-4-acetic acid, K' is N-methylarginine;

d is selected from 1, 2, 3, and 4;

$L_n$ is a linking group having the formula:

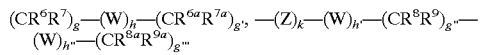

provided that g+h+g'+k+h'+g"+h"+g'" is other than 0;
W is independently selected at each occurrence from the group: O, S, NH, NHC(=O), C(=O)NH, C(=O), C(=O)O, OC(=O), NHC(=S)NH, NHC(=O)NH, SO$_2$, (OCH$_2$CH$_2$)$_s$, (CH$_2$CH$_2$O)$_{s'}$, (OCH$_2$CH$_2$CH$_2$)$_{s''}$, (CH$_2$CH$_2$CH$_2$O)$_t$, and (aa)$_{t'}$;
aa is, independently at each occurrence, an amino acid;
Z is selected from the group: aryl substituted with 0–3 R$^{10}$, C$_{3-10}$ cycloalkyl substituted with 0–3 R$^{10}$, and a 5–10 membered heterocyclic ring system containing 1–4 heteroatoms independently selected from N, S, and O and substituted with 0–3 R$^{10}$;
R$^6$, R$^{6a}$, R$^7$, R$^{7a}$, R$^8$, R$^{8a}$, R$^9$ and R$^{9a}$ are independently selected at each occurrence from the group: H, =O, COOH, SO$_3$H, PO$_3$H, C$_1$–C$_5$ alkyl substituted with 0–3 R$^{10}$, aryl substituted with 0–3 R$^{10}$, benzyl substituted with 0–3 R$^{10}$, and C$_1$–C$_5$ alkoxy substituted with 0–3 R$^{10}$, NHC(=O)R$^{11}$, C(=O)NHR$^{11}$, NHC(=O)NHR$^{11}$, NHR$^{11}$, R$^{11}$, and a bond to C$_h$;
R$^{10}$ is independently selected at each occurrence from the group: a bond to C$_h$, COOR$^{11}$, OH, NHR$^{11}$, SO$_3$H, PO$_3$H, aryl substituted with 0–3 R$^{11}$, C$_{1-5}$ alkyl substituted with 0–1 R$^{12}$, C$_{1-5}$ alkoxy substituted with 0–1 R$^{12}$, and a 5–10 membered heterocyclic ring system containing 1–4 heteroatoms independently selected from N, S, and O and substituted with 0–3 R$^{11}$;
R$^{11}$ is independently selected at each occurrence from the group: H, aryl substituted with 0–1 R$^{12}$, a 5–10 membered heterocyclic ring system containing 1–4 heteroatoms independently selected from N, S, and O and substituted with 0–1 R$^{12}$, C$_{3-10}$ cycloalkyl substituted with 0–1 R$^{12}$, polyalkylene glycol substituted with 0–1 R$^{12}$, carbohydrate substituted with 0–1 R$^{12}$, cyclodextrin substituted with 0–1 R$^{12}$, amino acid substituted with 0–1 R$^{12}$, polycarboxyalkyl substituted with 0–1 R$^{12}$, polyazaalkyl substituted with 0–1 R$^{12}$, peptide substituted with 0–1 R$^{12}$, wherein the peptide is comprised of 2–10 amino acids, and a bond to C$_h$;
R$^{12}$ is a bond to C$_h$;
k is selected from 0, 1, and 2;
h is selected from 0, 1, and 2;
h' is selected from 0, 1, 2, 3, 4, and 5;
h" is selected from 0, 1, 2, 3, 4, and 5;
g is selected from 0, 1, 2, 3, 4, 5, 6, 7, 8, 9, and 10;
g' is selected from 0, 1, 2, 3, 4, 5, 6, 7, 8, 9, and 10;
g" is selected from 0, 1, 2, 3, 4, 5, 6, 7, 8, 9, and 10;
g'" is selected from 0, 1, 2, 3, 4, 5, 6, 7, 8, 9, and 10;
s is selected from 0, 1, 2, 3, 4, 5, 6, 7, 8, 9, and 10;
s' is selected from 0, 1, 2, 3, 4, 5, 6, 7, 8, 9, and 10;
s" is selected from 0, 1, 2, 3, 4, 5, 6, 7, 8, 9, and 10;
t is selected from 0, 1, 2, 3, 4, 5, 6, 7, 8, 9, and 10;
t' is selected from 0, 1, 2, 3, 4, 5, 6, 7, 8, 9, and 10;
C$_h$ is a metal bonding unit having a formula selected from the group:

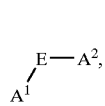
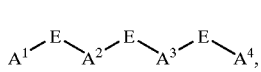

A$^1$, A$^2$, A$^3$, A$^4$, A$^5$, A$^6$, A$^7$, and A$^8$ are independently selected at each occurrence from the group: N, NR$^{13}$, NR$^{13}$R$^{14}$, S, SH, S(Pg), O, OH, PR$^{13}$, PR$^{13}$R$^{14}$, P(O)R$^{15}$R$^{16}$, and a bond to L$_n$;
E is a bond, CH, or a spacer group independently selected at each occurrence from the group: C$_1$–C$_{10}$ alkyl substituted with 0–3 R$^{17}$, aryl substituted with 0–3 R$^{17}$, C$_{3-10}$ cycloalkyl substituted with 0–3 R$^{17}$, heterocyclo-C$_{1-10}$ alkyl substituted with 0–3 R$^{17}$, wherein the heterocyclo group is a 5–10 membered heterocyclic ring system containing 1–4 heteroatoms independently selected from N, S, and O, C$_{6-10}$ aryl-C$_{1-10}$ alkyl substituted with 0–3 R$^{17}$, C$_{1-10}$ alkyl-C$_{6-10}$ aryl-substituted with 0–3, R$^{17}$, and a 5–10 membered heterocyclic ring system containing 1–4 heteroatoms independently selected from N, S, and O and substituted with 0–3 R$^{17}$;
R$^{13}$, and R$^{14}$ are each independently selected from the group: a bond to L$_n$, hydrogen, C$_1$–C$_{10}$ alkyl substituted with 0–3 R$^{17}$, aryl substituted with 0–3 R$^{17}$, C$_{1-10}$ cycloalkyl substituted with 0–3 R$^{17}$, heterocyclo-C$_{1-10}$ alkyl substituted with 0–3 R$^{17}$, wherein the heterocyclo group is a 5–10 membered heterocyclic ring system containing 1–4 heteroatoms independently selected from N, S, and O, C$_{6-10}$ aryl-C$_{1-10}$ alkyl substituted with 0–3 R$^{17}$, C$_{1-10}$ alkyl-C$_{6-10}$ aryl-substituted with 0–3 R$^{17}$, a 5–10 membered heterocyclic ring system containing 1–4 heteroatoms independently selected from N, S, and O and substituted with 0–3 R$^{17}$, and an electron, provided that when one of R$^{13}$ or R$^{14}$ is an electron, then the other is also an electron;
alternatively, R$^{13}$ and R$^{14}$ combine to form =C(R$^{20}$)(R$^{21}$);
R$^{15}$ and R$^{16}$ are each independently selected from the group: a bond to L$_n$, —OH, C$_1$–C$_{10}$ alkyl substituted with 0–3 R$^{17}$, C$_1$–C$_{10}$ alkyl substituted with 0–3 R$^{17}$, aryl substituted with 0–3 R$^{17}$, C$_{3-10}$ cycloalkyl substituted with 0–3 R$^{17}$, heterocyclo-C$_{1-10}$ alkyl substituted with 0–3 R$^{17}$, wherein the heterocyclo group is a 5–10 membered heterocyclic ring system containing 1–4 heteroatoms independently selected from N, S, and O, C$_{6-10}$ aryl-C$_{1-10}$ alkyl substituted with 0–3 R$^{17}$, C$_{1-10}$ alkyl-C$_{6-10}$ aryl-substituted with 0–3 R$^{17}$, and a 5–10 membered heterocyclic ring system containing 1–4 heteroatoms independently selected from N, S, and O and substituted with 0–3 R$^{17}$;
R$^{17}$ is independently selected at each occurrence from the group: a bond to L$_n$, =O, F, Cl, Br, I, —CF$_3$, —CN, —CO$_2$R$^{18}$, —C(=O)R$^{18}$, —C(=O)N(R$^{18}$)$_2$, —CHO, —CH$_2$OR$^{18}$, —OC(=O)R$^{18}$, —OC(=O)OR$^{18a}$, —OR$^{18}$, —OC(=O)N(R$^{18}$)$_2$, —NR$^{19}$C(=O)R$^{18}$, —NR$^{19}$C(=O)OR$^{18a}$, —NR$^{19}$C(=O)N(R$^{18}$)$_2$, —NR$^{19}$SO$_2$N(R$^{18}$)$_2$, —NR$^{19}$SO$_2$R$^{18a}$, —SO$_3$H, —SO$_2$R$^{18a}$, —SR$^{18}$, —S(=O)R$^{18a}$, —SO$_2$N(R$^{18}$)$_2$, —N(R$^{18}$)$_2$, —NHC(=S)NHR$^{18}$, =NOR$^{18}$, NO$_2$, —C(=O)NHOR$^{18}$, —C(=O)NHNR$^{18}$R$^{18a}$, —OCH$_2$CO$_2$H, 2-(1-morpholino)ethoxy, C$_1$–C$_5$ alkyl, C$_2$–C$_4$ alkenyl, C$_3$–C$_6$ cycloalkyl, C$_3$–C$_6$ cycloalkylmethyl, C$_2$–C$_6$ alkoxyalkyl, aryl substituted with 0–2 R$^{18}$, and a 5–10 membered heterocyclic ring system containing 1–4 heteroatoms independently selected from N, S, and O;

R$^{18}$, R$^{18a}$, and R$^{19}$ are independently selected at each occurrence from the group: a bond to L$_n$, H, C$_1$–C$_6$ alkyl, phenyl, benzyl, C$_1$–C$_6$ alkoxy, halide, nitro, cyano, and trifluoromethyl;

Pg is a thiol protecting group;

R$^{20}$ and R$^{21}$ are independently selected from the group: H, C$_1$–C$_{10}$ alkyl, —CN, —CO$_2$R$^{25}$, —C(=O)R$^{25}$, —C(=O)N(R$^{25}$)$_2$, C$_2$–C$_{10}$ 1-alkene substituted with 0–3 R$^{23}$, C$_2$–C$_{10}$ 1-alkyne substituted with 0–3 R$^{23}$, aryl substituted with 0–3 R$^{23}$, unsaturated 5–10 membered heterocyclic ring system containing 1–4 heteroatoms independently selected from N, S, and O and substituted with 0–3 R$^{23}$, and unsaturated C$_{3-10}$ carbocycle substituted with 0–3 R$^{23}$;

alternatively, R$^{20}$ and R$^{21}$, taken together with the divalent carbon radical to which they are attached form:

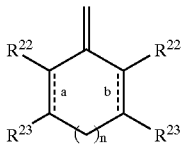

R$^{22}$ and R$^{23}$ are independently selected from the group: H, R$^{24}$, C$_1$–C$_{10}$ alkyl substituted with 0–3 R$^{24}$, C$_2$–C$_{10}$ alkenyl substituted with 0–3 R$^{24}$, C$_2$–C$_{10}$ alkynyl substituted with 0–3 R$^{24}$, aryl substituted with 0–3 R$^{24}$, a 5–10 membered heterocyclic ring system containing 1–4 heteroatoms independently selected from N, S, and O and substituted with 0–3 R$^{24}$, and C$_{3-10}$ carbocycle substituted with 0–3 R$^{24}$;

alternatively, R$^{22}$, R$^{23}$ taken together form a fused aromatic or a 5–10 membered heterocyclic ring system containing 1–4 heteroatoms independently selected from N, S, and O;

a and b indicate the positions of optional double bonds and n is 0 or 1;

R$^{24}$ is independently selected at each occurrence from the group: =O, F, Cl, Br, I, —CF$_3$, —CN, —CO$_2$R$^{25}$, —C(=O)R$^{25}$, —C(=O)N(R$^{25}$)$_2$, —N(R$^{25}$)$_3{}^+$, —CH$_2$OR$^{25}$, —OC(=O)R$^{25}$, —OC(=O)OR$^{25a}$, —OR$^{25}$, —OC(=O)N(R$^{25}$)$_2$, —NR$^{26}$C(=O)R$^{25}$, —NR$^{26}$C(=O)OR$^{25a}$, —NR$^{26}$C(=O)N(R$^{25}$)$_2$, —NR$^{26}$SO$_2$N(R$^{25}$)$_2$, —NR$^{26}$SO$_2$R$^{25a}$, —SO$_3$H, —SO$_2$R$^{25a}$, —SR$^{25}$, —S(=O)R$^{25a}$, —SO$_2$N(R$^{25}$)$_2$, —N(R$^{25}$)$_2$, =NOR$^{25}$, —C(=O)NHOR$^{25}$, —OCH$_2$CO$_2$H, and 2-(1-morpholino)ethoxy; and, R$^{25}$, R$^{25a}$, and R$^{26}$ are each independently selected at each occurrence from the group: hydrogen and C$_1$–C$_6$ alkyl;

and a pharmaceutically acceptable salt thereof.

In a still more preferred embodiment, the present invention provides a compound, wherein:

Q is a peptide selected from the group:

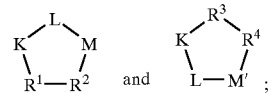

L is glycine;

M is L-aspartic acid;

M' is D-aspartic acid;

R$^1$ is L-valine, D-valine, D-lysine optionally substituted on the ε amino group with a bond to L$_n$ or L-lysine optionally substituted on the ε amino group with a bond to L$_n$;

R$^2$ is L-phenylalanine, D-phenylalanine, D-1-naphthylalanine, 2-aminothiazole-4-acetic acid, L-lysine optionally substituted on the e amino group with a bond to L$_n$ or tyrosine, the tyrosine optionally substituted on the hydroxy group with a bond to L$_n$;

R$^3$ is D-valine, D-phenylalanine, or L-lysine optionally substituted on the ε amino group with a bond to L$_n$;

R$^4$ is D-phenylalanine, D-tyrosine substituted on the hydroxy group with a bond to L$_n$, or L-lysine optionally substituted on the ε amino group with a bond to L$_n$;

provided that one of R$^1$ and R$^2$ in each Q is substituted with a bond to L$_n$, and further provided that when R$^2$ is 2-aminothiazole-4-acetic acid, K is N-methylarginine;

d is 1 or 2;

W is independently selected at each occurrence from the group: NHC(=O), C(=O)NH, C(=O), (CH$_2$CH$_2$O)$_{s'}$, and (CH$_2$CH$_2$CH$_2$O)$_t$;

R$^6$, R$^{6a}$, R$^7$, R$^{7a}$, R$^8$, R$^{8a}$, R$^9$, and R$^{9a}$ are independently selected at each occurrence from the group: H, NHC(=O)R$^{11}$, and a bond to C$_h$;

k is 0;

h", is selected from 0, 1, 2, and 3;

g is selected from 0, 1, 2, 3, 4, and 5;

g' is selected from 0, 1, 2, 3, 4, and 5;

g" is selected from 0, 1, 2, 3, 4, and 5;

g''' is selected from 0, 1, 2, 3, 4, and 5;

s' is 1 or 2;

t is 1 or 2;

C$_h$ is

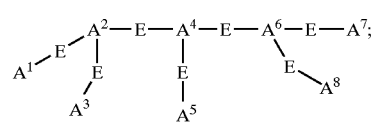

A$^1$ is selected from the group: OH, and a bond to L$_n$;

A$^2$, A$^4$, and A$^6$ are each N;

A$^3$, A$^5$, and A$^8$ are each OH;

$A^7$ is a bond to $L_n$ or NH-bond to $L_n$;
E is a $C_2$ alkyl substituted with 0–1 $R^{17}$;
  $R^{17}$ is =O;
alternatively, $C_h$ is

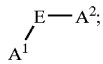

$A^1$ is $NH_2$ or $N=C(R^{20})(R^{21})$;
E is a bond;
$A^2$ is $NHR^{13}$;
  $R^{13}$ is a heterocycle substituted with $R^{17}$, the heterocycle being selected from pyridine and pyrimidine;
  $R^{17}$ is selected from a bond to $L_n$, $C(=O)NHR^{18}$, and $C(=O)R^{18}$;
  $R^{18}$ is a bond to $L_n$;
  $R^{24}$ is selected from the group: —$CO_2R^{25}$, —$OR^{25}$, —$SO_3H$, and —$N(R^{25})_2$;
    $R^{25}$ is independently selected at each occurrence from the group: hydrogen and methyl;
alternatively, $C_h$ is

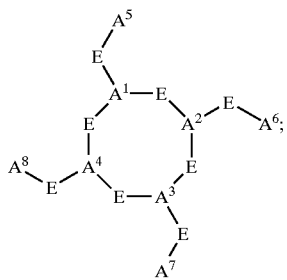

$A^1$, $A^2$, $A^3$, and $A^4$ are each N;
$A^5$, $A^6$, and $A^8$ are each OH;
$A^7$ is a bond to $L_n$;
E is a $C_2$ alkyl substituted with 0–1 $R^{17}$; and,
  $R^{17}$ is =O.

In another embodiment, the present invention provides compounds of the formulas Ia and Ib:

 (Ia);

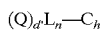 (Ib)

wherein, d is 1–3, d' is 2–4, $L_n$ is a linking group, $C_h$ is a metal chelator, and Q is a compound of formula IV or IVa:

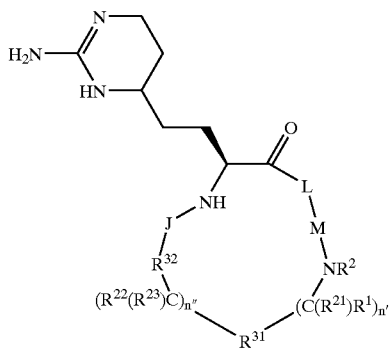

IV

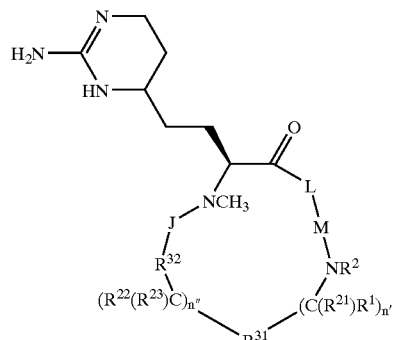

IVa or a pharmaceutically acceptable salt or prodrug form thereof, wherein:
  $R^{31}$ is a $C_6$–$C_{14}$ saturated, partially saturated, or aromatic carbocyclic ring system, substituted with 0–4 $R^{10}$ or $R^{10a}$, and optionally bearing a bond to $L_n$; a heterocyclic ring system, optionally substituted with 0–4 $R^{10}$ or $R^{10a}$, and optionally bearing a bond to $L_n$;
  $R^{32}$ is selected from: —$C(=O)$—; —$C(=S)$—; —$S(=O)_2$—; —$S(=O)$—; and —$P(=Z)(ZR^{13})$—;
  Z is S or O;
  n" and n' are independently 0–2;
  $R^1$ and $R^{22}$ are independently selected from the following groups: H, =O, F, Cl, Br, I, —$CF_3$, —CN, —$CO_2R^{13}$, —$C(=O)R^{13}$, —$C(=O)N(R^{13})_2$, —CHO, —$CH_2OR^{13}$, —$OC(=O)R^{13}$, —$OC(=O)OR^{13a}$, —$OR^{13}$, —$OC(=O)N(R^{13})_2$, —$NR^{13}C(=O)R^{13}$, —$NR^{14}C(=O)OR^{13a}$, —$NR^{13}C(=O)N(R^{13})_2$, —$NR^{14}SO_2N(R^{13})_2$, —$NR^{14}SO_2R^{13a}$, —$SO_3H$, —$SO_2R^{13a}$, —$SR^{13}$, —$S(=O)R^{13a}$, —$SO_2N(R^{13})_2$, —$N(R^{13})_2$, —$NHC(=NH)NHR^{13}$, —$C(=NH)NHR^{13}$, =$NOR^{13}$, $NO_2$, —$C(=O)NHOR^{13}$, —$C(=O)NHNR^{13}R^{13a}$, —$OCH_2CO_2H$, 2-(1-morpholino)ethoxy, $C_1$–$C_8$ alkyl substituted with 0–2 $R^{11}$; $C_2$–$C_8$ alkenyl substituted with 0–2 $R^{11}$; $C_2$–$C_8$ alkynyl substituted with 0–2 $R^{11}$; $C_3$–$C_{10}$ cycloalkyl substituted with 0–2 $R^{11}$; a bond to $L_n$; aryl substituted with 0–2 $R^{12}$; and a 5–10-membered heterocyclic ring system containing 1–4 heteroatoms independently selected from N, S, and O, said heterocyclic ring being substituted with 0–2 $R^{12}$;
  $R^1$ and $R^{21}$ can alternatively join to form a 3–7 membered carbocyclic ring substituted with 0–2 $R^{12}$;
  when n' is 2, $R^1$ or $R^{21}$ can alternatively be taken together with $R^1$ or $R^{21}$ on an adjacent carbon atom to form a direct bond, thereby to form a double or triple bond between said carbon atoms;
  $R^{21}$ and $R^{23}$ are independently selected from: hydrogen; $C_1$–$C_4$ alkyl, optionally substituted with 1–6 halogen; and benzyl;
  $R^{22}$ and $R^{23}$ can alternatively join to form a 3–7 membered carbocyclic ring substituted with 0–2 $R^{12}$;
  when n" is 2, $R^{22}$ or $R^{23}$ can alternatively be taken together with $R^{22}$ or $R^{23}$ on an adjacent carbon atom to form a direct bond, thereby to form a double or triple bond between the adjacent carbon atoms;
  $R^1$ and $R^2$, where $R^{21}$ is H, can alternatively join to form a 5–8 membered carbocyclic ring substituted with 0–2 $R^{12}$;
  $R^{11}$ is selected from one or more of the following: =O, F, Cl, Br, I, —$CF_3$, —CN, —$CO_2R_{13}$, —$C(=O)R^{13}$, —C(=O)N(R$^{13}$)$_2$, —CHO, —CH$_2$OR$^{13}$, —OC(=O)R$^{13}$, —OC(=O)OR$^{13a}$, —OR$^{13}$, —OC(=O)N(R$^{13}$)$_2$, —NR$^{13}$C(=O)R$^{13}$, —NR$^{14}$C(=O)OR$^{13a}$, —NR$^{13}$C(=O)N(R$^{13}$)$_2$, —NR$^{14}$SO$_2$N(R$^{13}$)$_2$, —NR$^{14}$SO$_2$R$^{13a}$, —SO$_3$H, —SO$_2$R$^{13a}$, —SR$^{13}$, —S(=O)R$^{13a}$, —SO$_2$N(R$^{13}$)$_2$, —N(R$^{13}$)$_2$, —NHC(=NH)NHR$^{13}$, —C(=NH)NHR$^{13}$, =NOR$^{13}$, NO$_2$, —C(=O)NHOR$^{13}$, —C(=O)NHNR$^{13}$R$^{13a}$, —OCH$_2$CO$_2$H, 2-(1-morpholino)ethoxy, C$_1$–C$_5$ alkyl, C$_2$–C$_4$ alkenyl, C$_3$–C$_6$ cycloalkyl, C$_3$–C$_6$ cycloalkylmethyl, C$_2$–C$_6$ alkoxyalkyl, C$_3$–C$_6$ cycloalkoxy, C$_1$–C$_4$ alkyl (alkyl being substituted with 1–5 groups selected independently from: —NR$^{13}$R$^{14}$, —CF$_3$, NO$_2$, —SO$_2$R$^{13a}$, or —S(=O)R$^{13a}$), aryl substituted with 0–2 R$^{12}$, and a 5–10-membered heterocyclic ring system containing 1–4 heteroatoms independently selected from N, S, and O, said heterocyclic ring being substituted with 0–2 R$^{12}$;

R$^{12}$ is selected from one or more of the following: phenyl, benzyl, phenethyl, phenoxy, benzyloxy, halogen, hydroxy, nitro, cyano, C$_1$–C$_5$ alkyl, C$_3$–C$_6$ cycloalkyl, C$_3$–C$_6$ cycloalkylmethyl, C$_7$–C$_{10}$ arylalkyl, C$_1$–C$_5$ alkoxy, —CO$_2$R$^{13}$, —C(=O)NHOR$^{13a}$, —C(=O)NHN(R$^{13}$)$_2$, =NOR$^{13}$, —B(R$^{34}$)(R$^{35}$), C$_3$–C$_6$ cycloalkoxy, —OC(=O)R$^{13}$, —C(=O)R$^{13}$, —OC(=O)OR$^{13a}$, —OR$^{13}$, —(C$_1$–C$_4$ alkyl)-OR$^{13}$, —N(R$^{13}$)$_2$, —OC(=O)N(R$^{13}$)$_2$, —NR$^{13}$C(=O)R$^{13}$, —NR$^{13}$C(=O)OR$^{13a}$, —NR$^{13}$C(=O)N(R$^{13}$)$_2$, —NR$^{13}$SO$_2$N(R$^{13}$)$_2$, —NR$^{13}$SO$_2$R$^{13a}$, —SO$_3$H, SO$_2$R$^{13a}$, —S(=O)R$^{13a}$, —SR$^{13}$, —SO$_2$N(R$^{13}$)$_2$, C$_2$–C$_6$ alkoxyalkyl, methylenedioxy, ethylenedioxy, C$_1$–C$_4$ haloalkyl, C$_1$–C$_4$ haloalkoxy, C$_1$–C$_4$ alkylcarbonyloxy, C$_1$–C$_4$ alkylcarbonyl, C$_1$–C$_4$ alkylcarbonylamino, —OCH$_2$CO$_2$H, 2-(1-morpholino)ethoxy, and C$_1$–C$_4$ alkyl (alkyl being substituted with —N(R$^{13}$)$_2$, —CF$_3$, NO$_2$, or —S(=O) R$^{13a}$);

R$^{13}$ is selected independently from: H, C$_1$–C$_{10}$ alkyl, C$_3$–C$_{10}$ cycloalkyl, C$_4$–C$_{12}$ alkylcycloalkyl, aryl, —(C$_1$–C$_{10}$ alkyl)aryl, and C$_3$–C$_{10}$ alkoxyalkyl;

R$^{13a}$ is C$_1$–C$_{10}$ alkyl, C$_3$–C$_{10}$ cycloalkyl, C$_4$–C$_{12}$ alkylcycloalkyl, aryl, —(C$_1$–C$_{10}$ alkyl)aryl, or C$_3$–C$_{10}$ alkoxyalkyl;

when two R$^{13}$ groups are bonded to a single N, said R$^{13}$ groups may alternatively be taken together to form —(CH$_2$)$_{2-5}$— or —(CH$_2$)O(CH$_2$)—;

R$^{14}$ is OH, H, C$_1$–C$_4$ alkyl, or benzyl;

R$^2$ is H or C$_1$–C$_8$ alkyl;

R$^{10}$ and R$^{10a}$ are selected independently from one or more of the following: phenyl, benzyl, phenethyl, phenoxy, benzyloxy, halogen, hydroxy, nitro, cyano, C$_1$–C$_5$ alkyl, C$_3$–C$_6$ cycloalkyl, C$_3$–C$_6$ cycloalkylmethyl, C$_7$–C$_{10}$ arylalkyl, C$_1$–C$_5$ alkoxy, —CO$_2$R$^{13}$, —C(=O)N(R$^{13}$)$_2$, —C(=O)NHOR$^{13a}$, —C(=O)NHN(R$^{13}$)$_2$, =NOR$^{13}$, —B(R$^{34}$)(R$^{35}$), C$_3$–C$_6$ cycloalkoxy, —OC(=O)R$^{13}$, —C(=O)R$^{13}$, —OC(=O)OR$^{13a}$, —OR$^{13}$, —(C$_1$–C$_4$ alkyl)-OR$^{13}$, —N(R$^{13}$)$_2$, —OC(=O)N(R$^{13}$)$_2$, —NR$^{13}$C(=O)R$^{13}$, —NR$^{13}$C(=O)OR$^{13a}$, —NR$^{13}$C(=O)N(R$^{13}$)$_2$, —NR$^{13}$SO$_2$N(R$^{13}$)$_2$, —NR$^{13}$SO$_2$R$^{13a}$, —SO$_3$H, —SO$_2$R$^{13a}$, —S(=O)R$^{13a}$, —SR$^{13}$, —SO$_2$N(R$^{13}$)$_2$, C$_2$–C$_6$ alkoxyalkyl, methylenedioxy, ethylenedioxy, C$_1$–C$_4$ haloalkyl (including —C$_v$F$_w$ where v=1 to 3 and w=1 to (2v+1)), C$_1$–C$_4$ haloalkoxy, C$_1$–C$_4$ alkylcarbonyloxy, C$_1$–C$_4$ alkylcarbonyl, C$_1$–C$_4$ alkylcarbonylamino, —OCH$_2$CO$_2$H, 2-(1-morpholino)ethoxy, and C$_1$–C$_4$ alkyl (alkyl being substituted with —N(R$^{13}$)$_2$, —CF$_3$, NO$_2$, or —S(=O)R$^{13a}$);

J is β-Ala or an L-isomer or D-isomer amino acid of structure —N(R$^3$)C(R$^4$)(R$^5$)C(=O)—, wherein:

R$^3$ is H or C$_1$–C$_8$ alkyl;

R$^4$ is H or C$_1$–C$_3$ alkyl;

R$^5$ is selected from: H, =O, F, Cl, Br, I, —CF$_3$, —CN, —CO$_2$R$^{13}$, —C(=O)R$^{13}$, —C(=O)N(R$^{13}$)$_2$, —CHO, —CH$_2$OR$^{13}$, —OC(=O)R$^{13}$, OC(=O)OR$^{13a}$, —OR$^{13}$, —OC(=O)N(R$^{13}$)$_2$, —NR$^{13}$C(=O)R$^{13}$, —NR$^{14}$C(=O)OR$^{13a}$, —NR$^{13}$C(=O)N(R$^{13}$)$_2$, —NR$^{14}$SO$_2$N(R$^{13}$)$_2$, —NR$^{14}$SO$_2$R$^{13a}$, —SO$_3$H, —SO$_2$R$^{13a}$, —SR$^{13}$, —S(=O)R$^{13a}$, —SO$_2$N(R$^{13}$)$_2$, —N(R$^{13}$)$_2$, —NHC(=NH)NHR$^{13}$, —C(=NH)NHR$^{13}$, =NOR$^{13}$, NO$_2$, —C(=O)NHOR$^{13}$, —C(=O)NHNR$^{13}$R$^{13a}$, =NOR$^{13}$, —B(R$^{34}$)(R$^{35}$), —OCH$_2$CO$_2$H, 2-(1-morpholino)ethoxy, —SC(=NH)NHR$^{13}$, N$_3$, —Si(CH$_3$)$_3$, (C$_1$–C$_5$ alkyl)NHR$^{16}$C$_1$–C$_8$ alkyl substituted with 0–2 R$^{11}$; C$_2$–C$_8$ alkenyl substituted with 0–2 R$^{11}$; C$_2$–C$_{10}$ alkynyl substituted with 0–2 R$^{11}$; C$_3$–C$_{10}$ cycloalkyl substituted with 0–2 R$^{11}$; a bond to L$_n$; aryl substituted with 0–2 R$^{12}$; and a 5–10-membered heterocyclic ring system containing 1–4 heteroatoms independently selected from N, S, or O, said heterocyclic ring being substituted with 0–2 R$^{12}$;

—(C$_0$–C$_6$ alkyl)X;

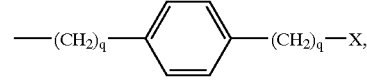

where q is independently 0 or 1;

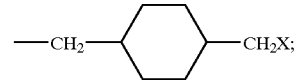

—(CH$_2$)$_m$S(O)$_{p'}$(CH$_2$)$_2$X, where m=1,2 and p'=0–2;
wherein X is defined below; and
R$^3$ and R$^4$ may also be taken together to form

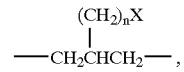

where n is 0 or 1
and X is w

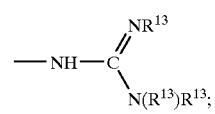

R$^3$ and R$^5$ can alternatively be taken together to form —(CH$_2$)$_t$— or —CH$_2$S(O)$_{p'}$C(CH$_3$)$_2$—, where t=2–4 and p'=0–2; or R$^4$ and R$^5$ can alternatively be taken together to form —(CH$_2$)$_u$—, where u=2–5;

R$^{16}$ is selected from: an amine protecting group; 1–2 amino acids; and 1–2 amino acids substituted with an amine protecting group;

L is —Y(CH$_2$)$_v$C(=O)—, wherein:

Y is NH, N(C$_1$–C$_3$ alkyl), O, or S; and v=1 or 2;

M is a D-isomer or L-isomer amino acid of structure

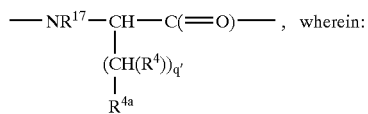

q' is 0–2;
$R^{17}$ is H, $C_1$–$C_3$ alkyl;
$R^{4a}$ is selected from: —$CO_2R^{13}$, —$SO_3R^{13}$, —$SO_2NHR^{14}$, —$B(R^{34})(R^{35})$, —$NHSO_2CF_3$, —$CONHNHSO_2CF_3$, —$PO(OR^{13})_2$, —$PO(OR^{13})R^{13}$, —$SO_2NH$-heteroaryl (said heteroaryl being 5–10-membered and having 1–4 heteroatoms selected independently from N, S, or O), —$SO_2NH$-heteroaryl (said heteroaryl being 5–10-membered and having 1–4 heteroatoms selected independently from N, S, or O), —$SO_2NHCOR^{13}$, —$CONHSO_2R^{13a}$, —$CH_2CONHSO_2R^{13a}$, —$NHSO_2NHCOR^{13a}$, —$NHCONHSO_2R^{13a}$, and —$SO_2NHCONHR^{13}$;

$R^{34}$ and $R^{35}$ are independently selected from: —OH, —F, —$N(R^{13})_2$, and $C_1$–$C_8$-alkoxy; and
$R^{34}$ and $R^{35}$ can alternatively be taken together form: a cyclic boron ester where said chain or ring contains from 2 to 20 carbon atoms and, optionally, 1–4 heteroatoms independently selected from N, S, or O; a divalent cyclic boron amide where said chain or ring contains from 2 to 20 carbon atoms and, optionally, 1–4 heteroatoms independently selected from N, S, or O; and a cyclic boron amide-ester where said chain or ring contains from 2 to 20 carbon atoms and, optionally, 1–4 heteroatoms independently selected from N, S, or O.

In another preferred embodiment, the present invention provides compounds of Formula V or Va:

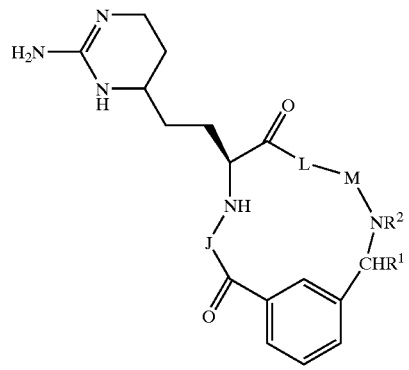

V

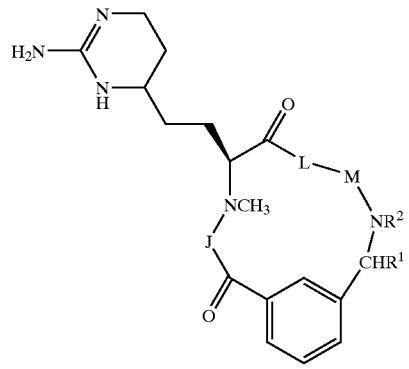

Va wherein:
the shown phenyl ring in formula (II) is optionally substituted with 0–3 $R^{10}$, and may optionally bear a bond to $L_n$;

$R^{10}$ is selected independently from: H, $C_1$–$C_8$ alkyl, phenyl, halogen, and $C_1$–$C_4$ alkoxy;
$R^1$ is selected from H, $C_1$–$C_4$ alkyl, phenyl, benzyl, phenyl-($C_1$–$C_4$)alkyl, and a bond to $L_n$;
$R^2$ is H or methyl;
$R^{13}$ is selected independently from: H, $C_1$–$C_{10}$ alkyl, $C_3$–$C_{10}$ cycloalkyl, $C_4$–$C_{12}$ alkylcycloalkyl, aryl, —($C_1$–$C_{10}$ alkyl)aryl, and $C_3$–$C_{10}$ alkoxyalkyl;
$R^{13a}$ is selected from $C_1$–$C_{10}$ alkyl, $C_3$–$C_{10}$ cycloalkyl, $C_4$–$C_{12}$ alkylcycloalkyl, aryl, —($C_1$–$C_{10}$ alkyl)aryl, and $C_3$–$C_{10}$ alkoxyalkyl;
when two $R^{13}$ groups are bonded to a single N, the $R^{13}$ groups alternatively are taken together to form —$(CH_2)_{2-5}$— or —$(CH_2)O(CH_2)$—;
$R^{14}$ is selected from OH, H, $C_1$–$C_4$ alkyl, and benzyl;
J is β-Ala or an L-isomer or D-isomer amino acid of structure —$N(R^3)C(R^4)(R^5)C(=O)$—, wherein:
$R^3$ is H or $CH_3$;
$R^4$ is H or $C_1$–$C_3$ alkyl;
$R^5$ is selected from H, $C_1$–$C_8$ alkyl, $C_3$–$C_6$ cycloalkyl, $C_3$–$C_6$ cycloalkylmethyl, $C_1$–$C_6$ cycloalkylethyl, phenyl, phenylmethyl, $CH_2OH$, $CH_2SH$, $CH_2OCH_3$, $CH_2SCH_3$, $CH_2CH_2SCH_3$, $(CH_2)_sNH_2$, —$(CH_2)_sNHC(=NH)(NH_2)$, and —$(CH_2)_sNHR^{16}$, where s=3–5, or a bond to $L_n$;
$R^3$ and $R^5$ alternatively are taken together to form —$CH_2CH_2CH_2$—;
$R^4$ and $R^5$ alternatively are taken together to form —$(CH_2)_u$—, where u=2–5;
$R^{16}$ is selected from: an amine protecting group; 1–2 amino acids; or 1–2 amino acids substituted with an amine protecting group;
L is —$Y(CH_2)_vC(=O)$—, wherein:
Y is NH, O, or S; and v=1,2;
M is a D-isomer or L-isomer amino acid of structure

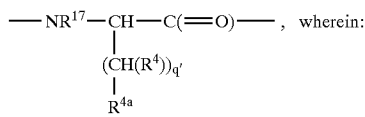

q' is 0–2;
$R^{17}$ is H or $C_1$–$C_3$ alkyl;
$R^{4a}$ is selected from: —$CO_2R^{13}$, —$SO_3R^{13}$, —$SO_2NHR^{14}$, —$B(R^{34})(R^{35})$, —$NHSO_2CF_3$, —$CONHNHSO_2CF_3$, —$PO(OR^{13})_2$, —$PO(OR^{13})R^{13}$, —$SO_2NH$-heteroaryl (said heteroaryl being 5–10-membered and having 1–4 heteroatoms selected independently from N, S, or O), and —$SO_2NH$-heteroaryl (the heteroaryl being 5–10-membered and having 1–4 heteroatoms selected independently from N, S, or O), —$SO_2NHCOR^{13}$, —$CONHSO_2R^{13a}$, —$CH_2CONHSO_2R^{13a}$, —$NHSO_2NHCOR^{13a}$, —$NHCONHSO_2R^{13a}$, and —$SO_2NHCONHR^{13}$.

In another more preferred embodiment, the present invention provides compounds of Formula (V) wherein:
the phenyl ring in formula (V) bears a bond to $L_n$;
$R^1$ and $R^2$ are independently selected from H, methyl;
J is selected from D-Val, D-2-aminobutyric acid, D-Leu, D-Ala, Gly, D-Pro, D-Ser, D-Lys, β-Ala, Pro, Phe, NMeGly, D-Nle, D-Phg, D-Ile, D-Phe, D-Tyr, Ala, $N^\epsilon$-p-azidobenzoyl-D-Lys, $N^\epsilon$-p-benzoylbenzoyl-D-Lys, $N^\epsilon$-tryptophanyl-D-Lys, $N^\epsilon$-o-benzoylbenzoyl-D-Lys, $N^\epsilon$-p-acetylbenzoyl-D-Lys, $N^\epsilon$-dansyl-D-Lys, $N^\epsilon$-glycyl-D-Lys, $N^\epsilon$-glycyl-p-benzoylbenzoyl-D-Lys, N$^\epsilon$-p-phenylbenzoyl-D-Lys, N$^\epsilon$-m-benzoylbenzoyl-D-Lys, and N$^\epsilon$-o-benzoylbenzoyl-D-Lys;

L is selected from Gly, β-Ala, and Ala; and

M is selected from Asp, αMeAsp, βMeasp, NMeAsp, and D-Asp.

In another preferred embodiment, $C_h$ is selected from the group:

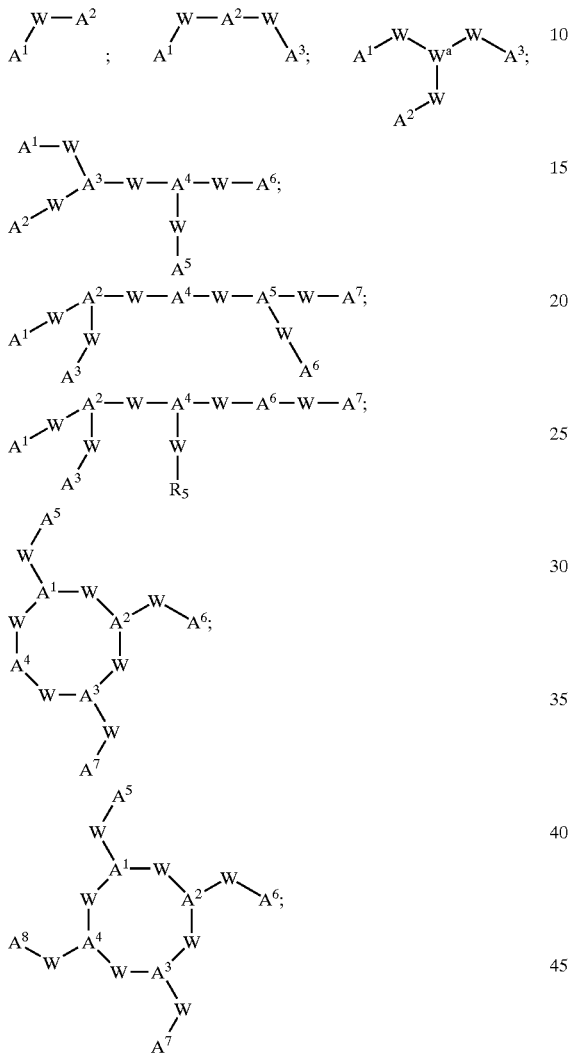

wherein:

$A^1$, $A^2$, $A^3$, $A^4$, $A^5$, $A^6$, $A^7$, and $A^8$ are independently selected at each occurrence from the group: $NR^{40}R^{41}$, S, SH, S(Pg), and OH;

W is a bond, CH, or $C_1$–$C_3$ alkyl substituted with 0–3 $R^{52}$;

$W^a$ is a methylene group or a $C_3$–$C_6$ carbocycle;

$R^{40}$, $R^{41}$, $R^{42}$, $R^{43}$, and $R^{44}$ are each independently selected from the group: a bond to $L_n$, hydrogen, $C_1$–$C_{10}$ alkyl substituted with 0–3 $R^{52}$, and an electron, provided that when one of $R^{40}$ or $R^{41}$ is an electron, then the other is also an electron, and provided that when one of $R^{42}$ or $R^{43}$ is an electron, then the other is also an electron;

alternatively, $R^{40}$ and $R^{41}$ combine to form, =C($C_1$–$C_3$ alkyl)($C_1$–$C_3$ alkyl);

$R^{52}$ is independently selected at each occurrence from the group: a bond to $L_n$, =O, F, Cl, Br, I, —CF$_3$, —CN, —CO$_2R^{53}$, —C(=O)$R^{53}$, —C(=O)N($R^{53}$)$_2$, —CHO, —CH$_2$O$R^{53}$, —OC(=O)$R^{53}$, —OC(=O)O$R^{53a}$, —O$R^{53}$, —OC(=O)N($R^{53}$)$_2$, —NR$^{53}$C(=O)$R^{53}$, —NR$^{54}$C(=O)O$R^{53a}$, —NR$^{53}$C(=O)N($R^{53}$)$_2$, —NR$^{54}$SO$_2$N($R^{53}$)$_2$, —NR$^{54}$SO$_2R^{53a}$, —SO$_3$H, —SO$_2R^{53a}$, —S$R^{53}$, —S(=O)$R^{53a}$, —SO$_2$N($R^{53}$)$_2$, —N($R^{53}$)$_2$, —NHC(=NH)NHR$^{53}$, —C(=NH)NHR$^{53}$, =NOR$^{53}$, NO$_2$, —C(=O)NHOR$^{53}$, —C(=O)NHNR$^{53}R^{53a}$, —OCH$_2$CO$_2$H, and 2-(1-morpholino)ethoxy;

$R^{53}$, $R^{53a}$, and $R^{54}$ are independently selected at each occurrence from the group: a bond to $L_n$, and $C_1$–$C_6$ alkyl.

In another more preferred embodiment, the present invention provides a compound of Formula VI:

$$(QL_n)_d C_h,$$

wherein:

d is 1; and $C_h$ is:

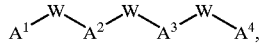

$A^1$ and $A^4$ are SH or SPg;

$A^2$ and $A^3$ are $NR^{41}$;

W is independently selected from the group: CHR$^{52}$, CH$_2$CHR$^{52}$, CH$_2$CH$_2$CHR$^{52}$ and CHR$^{52}$C=O; and, $R^{41}$ and $R^{52}$ are independently selected from hydrogen and a bond to $L_n$, alternatively, $C_h$ is:

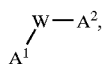

$A^1$ is NH$_2$ or N=C($C_1$–$C_3$ alkyl)($C_1$–$C_3$ alkyl);

W is a bond; and, $A^2$ is NHR$^{40}$, wherein $R^{40}$ is heterocycle substituted with $R^{52}$, wherein the heterocycle is selected from the group:

pyridine, pyrazine, proline, furan, thiofuran, thiazole, and diazine, and $R^{52}$ is a bond to $L_n$.

In another more preferred embodiment, the present invention provides a compound of Formula VI, wherein d is 1;

$C_h$ is:

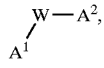

$A^1$ is NH$_2$ or N=C($C_1$–$C_3$ alkyl)($C_1$–$C_3$ alkyl);

W is a bond; and, $A^2$ is NHR$^{40}$, wherein $R^{40}$ is heterocycle substituted with $R^{52}$, wherein the heterocycle is selected from pyridine and thiazole, and $R^{52}$ is a bond to $L_n$.

In another preferred embodiment, Ln is:

a bond between Q and $C_h$; or,

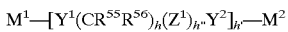

wherein:

$M^1$ is $-[(CH_2)_g Z^1]_{g'}-(CR^{55}R^{56})_{g''}-$;

$M^2$ is $-(CR^{55}R^{56})_{g''}-[Z^1(CH_2)_g]_{g'}-$;

g is independently 0–10;

g' is independently 0–1;

g" is 0–10;

h is 0–10;

h' is 0–10;

h" is 0–1

$Y^1$ and $Y^2$, at each occurrence, are independently selected from: a bond, O, $NR^{56}$, C=O, C(=O)O, OC(=O)O, C(=O)NH—, C=$NR^{56}$, S, SO, $SO_2$, $SO_3$, NHC(=O), $(NH)_2C(=O)$, and $(NH)_2C=S$;

$Z^1$ is independently selected at each occurrence from a $C_6$–$C_{14}$ saturated, partially saturated, or aromatic carbocyclic ring system, substituted with 0–4 $R^{57}$; a heterocyclic ring system, optionally substituted with 0–4 $R^{57}$;

$R^{55}$ and $R^{56}$ are independently selected at each occurrence from: hydrogen; $C_1$–$C_{10}$ alkyl substituted with 0–5 $R^{57}$; and ($C_1$–$C_{10}$ alkyl)aryl wherein the aryl is substituted with 0–5 $R^{57}$;

$R^{57}$ is independently selected at each occurrence from the group: hydrogen, OH, $NHR^{58}$, C(=O)$R^{58}$, OC(=O)$R^{58}$, OC(=O)O$R^{58}$, C(=O)O$R^{58}$, C(=O)N$R^{58}$—, C≡N, S$R^{58}$, SO$R^{58}$, $SO_2R^{58}$, NHC(=O)$R^{58}$, NHC(=O)NH$R^{58}$, NHC(=S)NH$R^{58}$; or, alternatively, when attached to an additional molecule Q, $R^{57}$ is independently selected at each occurrence from the group: O, N$R^{58}$, C=O, C(=O)O, OC(=O)O, C(=O)N—, C=N$R^{58}$, S, SO, $SO_2$, $SO_3$, NHC(=O), $(NH)_2C(=O)$, and $(NH)_2C=S$; and, $R^{58}$ is independently selected at each occurrence from the group: hydrogen; $C_1$–$C_6$ alkyl; benzyl, and phenyl.

In another more preferred embodiment, Ln is:

$$-(CR^{55}R^{56})_{g''}-[Y^1(CR^{55}R^{56})_hY^2]_{h'}-(CR^{55}R^{56})_{g''}-,$$

wherein:

g" is 1–10;

h is 0–10;

h' is 1–10;

$Y^1$ and $Y^2$, at each occurrence, are independently selected from: a bond, O, $NR^{56}$, C=O, C(=O)O, OC(=O)O, C(=O)NH—, C=$NR^{56}$, S, SO, $SO_2$, $SO_3$, NHC(=O), $(NH)_2C(=O)$, and $(NH)_2C=S$;

$R^{55}$ and $R^{56}$ are independently selected at each occurrence from: hydrogen; $C_1$–$C_{10}$ alkyl substituted with 0–5 $R^{57}$; and ($C_1$–$C_{10}$ alkyl)aryl wherein the aryl is substituted with 0–5 $R^{57}$;

$R^{57}$ is independently selected at each occurrence from the group: hydrogen, OH, $NHR^{58}$, C(=O)$R^{58}$, OC(=O)$R^{58}$, OC(=O)O$R^{58}$, C(=O)O$R^{58}$, C(=O)N$R^{58}$—, C≡N, S$R^{58}$, SO$R^{58}$, $SO_2R^{58}$, NHC(=O)$R^{58}$, NHC(=O)NH$R^{58}$, and NHC(=S)NH$R^{58}$;

alternatively, when attached to an additional molecule Q, $R^{57}$ is independently selected at each occurrence from the group: O, N$R^{58}$, C=O, C(=O)O, OC(=O)O, C(=O)N—, C=N$R^{58}$, S, SO, $SO_2$, $SO_3$, NHC(=O), $(NH)_2C(=O)$, and $(NH)_2C=S$, and $R^{57}$ is attached to an additional molecule Q; and, $R^{58}$ is independently selected at each occurrence from the group: hydrogen; $C_1$–$C_6$ alkyl; benzyl, and phenyl.

In another more preferred embodiment, Ln is:

$$-(CR^{55}R^{56})_{g''}-[Y^1(CR^{55}R^{56})_hY^2]_{h'}-(CR^{55}R^{56})_{g''}-,$$

wherein:

g" is 1–5;

h is 0–5;

h' is 1–5;

$Y^1$ and $Y^2$, at each occurrence, are independently selected from: O, $NR^{56}$, C=O, C(=O)O, OC(=O)O, C(=O)NH—, C=$NR^{56}$, S, SO, $SO_2$, $SO_3$, NHC(=O), $(NH)_2C(=O)$, and $(NH)_2C=S$; and, $R^{55}$ and $R^{56}$ are independently selected at each occurrence from: hydrogen; $C_1$–$C_{10}$ alkyl; and ($C_1$–$C_{10}$ alkyl)aryl In another more preferred embodiment, Ln is:

$$-(CR^{55}R^{56})_{g''}-[Y^1(CR^{55}R^{56})_hY^2]_{h'}-(CR^{55}R^{56})_{g''}-,$$

wherein:

g" is 1–5;

h is 0–5;

h' is 1–5;

$Y^1$ and $Y^2$, at each occurrence, are independently selected from: O, $NR^{56}$, C=O, C(=O)O, OC(=O)O, C(=O)NH—, C=$NR^{56}$, S, NHC(=O), $(NH)_2C(=O)$, and $(NH)_2C=S$; and, $R^{55}$ and $R^{56}$ are each hydrogen.

In another embodiment, the present invention provides a novel compound of the formula:

$$C_h-L_n-(X^1X^2X^3X^4X^5)_d,$$

wherein:

$X^1$ is an amino acid independently selected from the group: threonine, serine, 3-hydroxyproline, and 4-hydroxyproline;

$X^2$ is cyArg;

$X^3$ and $X^4$ are amino acids independently selected at each occurrence from the group: proline, and homoproline;

$X^5$ is an amino acid independently selected from the group: lysine, ornithine, arginine, glutamine, and 2-amino-5-(2-imidazolin-2-ylamino)pentanoic acid;

d is selected from 1, 2, and 3;

$L_n$ is a linking group having the formula:

$$(CR^6R^7)_g-(W)_h-(CR^{6a}R^{7a})_{g'}-(W)_{h'}-(CR^8R^9)_{g''}-(W)_{h''}-(CR^{8a}R^{9a})_{g'''}-(W)_{h'''}$$

W is independently selected at each occurrence from the group: O, NH, NHC(=O), C(=O)NH, C(=O), C(=O)O, and OC(=O);

$R^6$, $R^{6a}$, $R^7$, $R^{7a}$, $R^8$, $R^{8a}$, $R^9$ and $R^{9a}$ are independently selected at each occurrence from the group: =O, COOH, $SO_3H$, $PO_3H$, $C_1$–$C_5$ alkyl substituted with 0–3 $R^{10}$, aryl substituted with 0–3 $R^{10}$, benzyl substituted with 0–3 $R^{10}$, and $C_1$–$C_5$ alkoxy substituted with 0–3 $R^{10}$, NHC(=O)$R^{11}$, C(=O)NH$R^{11}$, NHC(=O)NH$R^{11}$, NH$R^{11}$, $R^{11}$, and a bond to $C_h$;

$R^{10}$ is independently selected at each occurrence from the group: a bond to $C_h$, COO$R^{11}$, OH, NH$R^{11}$, $SO_3H$, $PO_3H$, aryl substituted with 0–3 $R^{11}$, $C_{1-5}$ alkyl substituted with 0–1 $R^{12}$, $C_{1-5}$ alkoxy substituted with 0–1 $R^{12}$, and a 5–10 membered heterocyclic ring system containing 1–4 heteroatoms independently selected from N, S, and O and substituted with 0–3 $R^{11}$;

$R^{11}$ is independently selected at each occurrence from the group: H, aryl substituted with 0–1 $R^{12}$, a 5–10 membered heterocyclic ring system containing 1–4 heteroatoms independently selected from N, S, and O and substituted with 0–1 $R^{12}$, $C_{3-10}$ cycloalkyl substituted with 0–1 $R^{12}$, and a bond to $C_h$;

$R^{12}$ is a bond to $C_h$;

h is selected from 0, 1, 2, 3, 4, and 5;
h' is selected from 0, 1, 2, 3, 4, and 5;
h" is selected from 0, 1, 2, 3, 4, and 5;
h'" is selected from 0, 1, 2, 3, 4, and 5;
g is selected from 0, 1, 2, 3, 4, 5, 6, 7, 8, 9, and 10;
g' is selected from 0, 1, 2, 3, 4, 5, 6, 7, 8, 9, and 10;
g" is selected from 0, 1, 2, 3, 4, 5, 6, 7, 8, 9, and 10;
g'" is selected from 0, 1, 2, 3, 4, 5, 6, 7, 8, 9, and 10;
$C_h$ is a metal bonding unit having the formula:

wherein:
$R^{13}$, and $R^{14}$ are each independently selected from the group: hydrogen, aryl substituted with 0–3 $R^{17}$, and a 5–10 membered heterocyclic ring system containing 1–4 heteroatoms independently selected from N, S, and O and substituted with 0–3 $R^{17}$;

$R^{15}$ and $R^{16}$ are both H, or combine to form =C($R^{20}$)($R^{21}$);

$R^{17}$ is independently selected at each occurrence from the group: a bond to $L_n$, F, Cl, Br, I, —$CF_3$, —CN, —$CO_2R^{18}$, —C(=O)$R^{18}$, —C(=O)N($R^{18}$)$_2$, —$CH_2OR^{18}$, —OC(=O)$R^{18}$, —OC(=O)O$R^{18}$, —$OR^{18}$, —$SO_2N(R^{18})_2$, $C_1$–$C_5$ alkyl, aryl substituted with 0–2 $R^{18}$, and a 5–10 membered heterocyclic ring system containing 1–4 heteroatoms independently selected from N, S, and O;

$R^{18}$ is independently selected at each occurrence from the group: a bond to $L_n$, H, $C_1$–$C_6$ alkyl, phenyl, and benzyl;

$R^{25}$, $R^{25a}$, and $R^{26}$ are each independently selected at each occurrence from the group: hydrogen and $C_1$–$C_6$ alkyl;

and a pharmaceutically acceptable salt thereof.

In a preferred embodiment, the present invention provides a compound, wherein:

$X^1$ is an amino acid independently selected from the group: threonine, and serine;

$X^2$ is cyArg;

$X^5$ is an amino acid independently selected from the group: lysine, 2-amino-5-(2-imidazolin-2-ylamino)pentanoic acid, and arginine;

W is independently selected at each occurrence from the group: O, N, NHC(=O), C(=O)NH, and C(=O);

$R^6$, $R^{6a}$, $R^7$, $R^{7a}$, $R^8$, $R^{8a}$, $R^9$ and $R^{9a}$ are independently selected at each occurrence from the group: =O, COOH, $SO_3H$, $PO_3H$, $C_1$–$C_5$ alkyl substituted with 0–1 $R^{10}$, aryl substituted with 0–1 $R^{10}$, benzyl substituted with 0–1 $R^{10}$, and $C_1$–$C_5$ alkoxy substituted with 0–1 $R^{10}$, NHC(=O)$R^{11}$, C(=O)NH$R^{11}$, NHC(=O)NH$R^{11}$, NH$R^{11}$, $R^{11}$, and a bond to $C_h$;

$R^{10}$ is independently selected at each occurrence from the group: a bond to $C_h$, COO$R^{11}$, OH, NH$R^{11}$, $SO_3H$, aryl substituted with 0–1 $R^{11}$, $C_{1-5}$ alkyl substituted with 0–1 $R^{12}$, $C_{1-5}$ alkoxy substituted with 0–1 $R^{12}$, and a 5–10 membered heterocyclic ring system containing 1–4 heteroatoms independently selected from N, S, and O and substituted with 0–3 $R^{11}$;

$R^{11}$ is independently selected at each occurrence from the group: H, aryl substituted with 0–1 $R^{12}$, a 5–10 membered heterocyclic ring system containing 1–4 heteroatoms independently selected from N, S, and O and substituted with 0–1 $R^{12}$, and a bond to $C_h$;

h is 0 or 1;
h' is 0 or 1;
$C_h$ is a metal bonding unit having the formula:

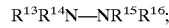

wherein:
$R^{17}$ is independently selected at each occurrence from the group: a bond to $L_n$, F, Cl, Br, I, —$CF_3$, —CN, —$CO_2R^{18}$, —C(=O)$R^{18}$, —C(=O)N($R^{18}$)$_2$, —$CH_2OR^{18}$, —OC(=O)$R^{18}$, —OC(=O)O$R^{18}$, —$OR^{18}$, and —$SO_2N(R^{18})_2$;

$R^{18}$ is independently selected at each occurrence from the group: a bond to $L_n$, H, and $C_1$–$C_6$ alkyl;

$R^{25}$ is independently selected at each occurrence from the group: hydrogen and $C_1$–$C_3$ alkyl;

In another more preferred embodiment, the present invention provides a compound, wherein:

$X^1$ is threonine;
$X^2$ is cyArg;
$X^5$ is arginine;
d is 1 or 2;
W is independently selected at each occurrence from the group: NHC(=O), C(=O)NH, and C(=O);

$R^6$, $R^{6a}$, $R^7$, $R^{7a}$, $R^8$, $R^{8a}$, $R^9$ and $R^{9a}$ are independently selected at each occurrence from the group: H benzyl substituted with 0–1 $R^{10}$, and a bond to $C_h$;

$R^{10}$ is OH;
h" is 0 or 1;
h'" is 0 or 1;
g is selected from 0, 1, 2, 3, 4, and 5;
g' is selected from 0, 1, 2, 3, 4, and 5;
g" is selected from 0, 1, 2, 3, 4, and 5;
g'" is selected from 0, 1, 2, 3, 4, and 5;
$C_h$ is a metal bonding unit having the formula:

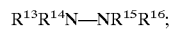

wherein:
$R^{13}$ is H;
$R^{14}$ is a heterocyclic ring system substituted with $R^{17}$, the heterocyclic ring system being selected from pyridine and pyrimidine;
$R^{17}$ is —C(=O)NH$R^{18}$;
$R^{18}$ is a bond to $L_n$;
$R^{25}$ is independently selected at each occurrence from the group: hydrogen and methyl.

In another preferred embodiment, the present invention provides a kit comprising a compound of the present invention and a container containing the compound.

In another embodiment, the present invention provides a novel diagnostic or therapeutic, an MRI contrast agent, or an X-ray contrast agent, comprising: a metal and a compound of the present invention, wherein:

when a diagnostic or therapeutic is present, the metal is, selected from: $^{99m}$Tc, $^{95}$Tc, $^{111}$In, $^{62}$Cu, $^{64}$Cu, $^{67}$Ga, $^{68}$Ga, $^{186}$Re, $^{188}$Re, $^{153}$Sm, $^{166}$Ho, $^{177}$Lu, $^{149}$Pm, $^{90}$Y, $^{212}$Bi, $^{103}$Pd, $^{109}$Pd, 159Gd, $^{140}$La, $^{198}$Au, $^{199}$Au, $^{169}$Yb, 175Yb, $^{165}$Dy, $^{166}$Dy, $^{67}$Cu, $^{105}$Rh, $^{111}$Ag, and $^{192}$Ir;

when an MRI contrast agent is present, the metal is selected from: Gd(III), Dy(III), Fe(III), and Mn(II); and, when an X-ray contrast agent is present, the metal is selected from: Re, Sm, Ho, Lu, Pm, Y, Bi, Pd, Gd, La, Au, Au, Yb, Dy, Cu, Rh, Ag, and Ir.

In another embodiment, the present invention provides a novel compound capable of being used in an ultrasound contrast composition, comprising: a targeting moiety and a surfactant and the compound has 0–1 linking groups between the targeting moiety and surfactant.

In another even more preferred embodiment, the compound is a targeting moiety of the present invention, wherein the —$L_n$—$C_h$ group is replaced by a group of the formula:

wherein:

$S_f$ is a surfactant which is a lipid or a compound of the formula:

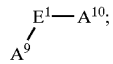

$A^9$ is $OR^{27}$;
$A^{10}$ is $OR^{27}$;
$R^{27}$ is $C(=O)C_{1-15}$ alkyl;
$E^1$ is $C_{1-4}$ alkylene substituted with 1–3 $R^{28}$;
$R^{28}$ is independently selected at each occurrence from the group: $R^{30}$, —$PO_3H$—$R^{30}$, =O, —$CO_2R^{29}$, —$C(=O)R^{29}$, —$CH_2OR^{29}$, —$OR^{29}$, and $C_1$–$C_5$ alkyl;
$R^{29}$ is independently selected at each occurrence from the group: $R^{30}$, H, $C_1$–$C_6$ alkyl, phenyl, and benzyl;
$R^{30}$ is a bond to $L_n$;
$L_n$ is a linking group having the formula:

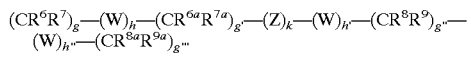

W is independently selected at each occurrence from the group: O, S, NH, NHC(=O), C(=O)NH, C(=O), C(=O)O, OC(=O), NHC(=S)NH, NHC(=O)NH, $SO_2$, $(OCH_2CH_2)_{20-200}$, $(CH_2CH_2O)_{20-200}$, $(OCH_2CH_2CH_2)_{20-200}$, $(CH_2CH_2CH_2O)_{20-200}$, and $(aa)_t$;
aa is independently at each occurrence an amino acid;
Z is selected from the group: aryl substituted with 0–3 $R^{10}$, $C_{3-10}$ cycloalkyl substituted with 0–3 $R^{10}$, and a 5–10 membered heterocyclic ring system containing 1–4 heteroatoms independently selected from N, S, and O and substituted with 0–3 $R^{10}$;
$R^6$, $R^{6a}$, $R^7$, $R^{7a}$, $R^8$, $R^{8a}$, $R^9$ and $R^{9a}$ are independently selected at each occurrence from the group: H, =O, $C_1$–$C_5$ alkyl substituted with 0–3 $R^{10}$, and $C_1$–$C_5$ alkoxy substituted with 0–3 $R^{10}$, and a bond to $S_f$;
$R^{10}$ is independently selected at each occurrence from the group: a bond to $S_f$, $COOR^{11}$, OH, $NHR^{11}$, $C_{1-5}$ alkyl substituted with 0–1 $R^{12}$, and $C_{1-5}$ alkoxy substituted with 0–1 $R^{12}$;
$R^{11}$ is independently selected at each occurrence from the group: H, aryl substituted with 0–1 $R^{12}$, $C_{3-10}$ cycloalkyl substituted with 0–1 $R^{12}$, amino acid substituted with 0–1 $R^{12}$, and a bond to $S_f$;
$R^{12}$ is a bond to $S_f$;
k is selected from 0, 1, and 2;
h is selected from 0, 1, and 2;
h' is selected from 0, 1, 2, 3, 4, and 5;
h'' is selected from 0, 1, 2, 3, 4, and 5;
g is selected from 0, 1, 2, 3, 4, and 5;
g' is selected from 0, 1, 2, 3, 4, and 5;
g'' is selected from 0, 1, 2, 3, 4, and 5;
g''' is selected from 0, 1, 2, 3, 4, and 5;
s is selected from 0, 1, 2, 3, 4, and 5;
s' is selected from 0, 1, 2, 3, 4, and 5;
s'' is selected from 0, 1, 2, 3, 4, and 5;
t is selected from 0, 1, 2, 3, 4, and 5;
t' is selected from 0, 1, 2, 3, 4, and 5;
and a pharmaceutically acceptable salt thereof.

In another even more preferred embodiment, the present invention provides a novel ultrasound contrast agent composition, comprising:

(a) a compound comprising: a targeting ligand of the present invention, a surfactant and a linking group between the targeting ligand and the surfactant;

(b) a parenterally acceptable carrier; and, (c) an echogenic gas.

In another still more preferred embodiment, the ultrasound contrast agent further comprises: 1,2-dipalmitoyl-sn-glycero-3-phosphotidic acid, 1,2-dipalmitoyl-sn-glycero-3-phosphatidylcholine, and N-(methoxypolyethylene glycol 5000 carbamoyl)-1,2-dipalmitoyl-sn-glycero-3-phosphatidylethanolamine.

In another further preferred embodiment, the echogenic gas is a $C_{2-5}$ perfluorocarbon.

In another even more preferred embodiment, the present; invention provides a novel therapeutic radiopharmaceutical composition, comprising:

(a) a therapeutic radiopharmaceutical of the present invention; and, (b) a parenterally acceptable carrier.

In another even more preferred embodiment, the present invention provides a novel diagnostic radiopharmaceutical composition, comprising:

(a) a diagnostic radiopharmaceutical, a MRI contrast agent, or a X-ray contrast agent of the present invention; and, (b) a parenterally acceptable carrier.

In another even more preferred embodiment, the present invention provides a novel therapeutic radiopharmaceutical composition, comprising: a radiolabelled targeting moiety, wherein the targeting moiety is a compound Q and the radiolabel is a therapeutic isotope selected from the group: $^{35}S$, $^{32}P$, $^{125}I$, $^{131}I$, and $^{211}At$.

In another further preferred embodiment, the present invention provides a novel therapeutic radiopharmaceutical composition, comprising: a radiolabelled targeting moiety, wherein the targeting moiety is a compound Q and the radiolabel is a therapeutic isotope which is $^{131}I$.

In another embodiment, the present invention provides diagnostic kits for the preparation of radiopharmaceuticals useful as imaging agents for cancer or imaging agents for imaging formation of new blood vessels. Diagnostic kits of the present invention comprise one or more vials containing the sterile, non-pyrogenic, formulation comprised of a predetermined amount of a reagent of the present invention, and optionally other components such as one or two ancillary, ligands, reducing agents, transfer ligands, buffers, lyophilization aids, stabilization aids, solubilization aids and bacteriostats. The inclusion of one or more optional components in the formulation will frequently improve the ease of synthesis of the radiopharmaceutical by the practicing end user, the ease of manufacturing the kit, the shelf-life of the kit, or the stability and shelf-life of the radiopharmaceutical. The inclusion of one or two ancillary ligands is required for diagnostic kits comprising, reagent comprising a hydrazine or hydrazone bonding moiety. The one or more vials that contain all or part of the formulation can independently be in the form of a sterile solution or a lyophilized solid.

In another embodiment, the present invention provides an arginine or arginine mimetic containing acyclic or cyclic peptide that targets a biological receptor, wherein the improvement comprises: replacement of the arginine or arginine mimetic with a group of formula IIIa or IIIb:

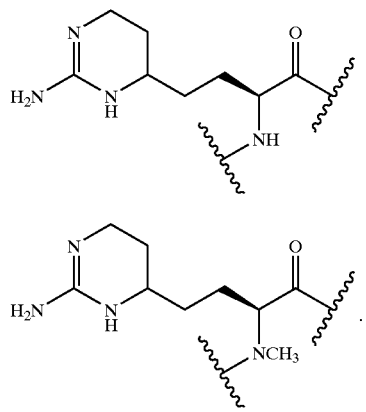

IIIa

IIIb

DEFINITIONS

The compounds herein described may have asymmetric centers. Unless otherwise indicated, all chiral, diastereomeric and racemic forms are included in the present invention. Many geometric isomers of olefins, C=N double bonds, and the like can also be present in the compounds described herein, and all such stable isomers are contemplated in the present invention. It will be m appreciated that compounds of the present invention contain asymmetrically substituted carbon atoms, and may be isolated in optically active or racemic forms. It is well known in the art how to prepare optically active forms, such as by resolution of racemic forms or by synthesis from optically active starting materials. Two distinct isomers (cis and trans) of the peptide bond are known to occur; both can also be present in the compounds described herein, and all such stable isomers are contemplated in the present invention. The D and L-isomers of a particular amino acid are designated herein using the conventional 3-letter abbreviation of the amino acid, as indicated by the following examples: D-Leu, or L-Leu.

When any variable occurs more than one time in any substituent or in any formula, its definition on each occurrence is independent of its definition at every other occurrence. Thus, for example, if a group is shown to be substituted with 0–2 $R^{52}$, then said group may optionally be substituted with up to two $R^{52}$, and $R^{52}$ at each occurrence is selected independently from the defined list of possible $R^{52}$. Also, by way of example, for the group —N($R^{53}$)$_2$, each of the two $R^{53}$ substituents on N is independently selected from the defined list of possible $R^{53}$. Combinations of substituents and/or variables are permissible only if such combinations result in stable compounds. When a bond to a substituent is shown to cross the bond connecting two atoms in a ring, then such substituent may be bonded to any atom on the ring.

As used herein, the term "amino protecting group" (or "N-protected") refers to any group known in the art of organic synthesis for the protection of amine groups. As used herein, the term "amino protecting group reagent" refers to any reagent known in the art of organic synthesis. for the protection of amine groups that may be reacted with an amine to provide an amine protected with an amine-protecting group. Such amine protecting groups include those listed in Greene and Wuts, "Protective Groups in Organic Synthesis" John Wiley & Sons, New York (1991) and "The Peptides: Analysis, Synthesis, Biology, Vol. 3, Academic Press, New York, (1981), the disclosure of which is hereby incorporated by reference. Examples of amine protecting groups include, but are not limited to, the following: 1) acyl types such as formyl, trifluoroacetyl (TFA), phthalyl, and p-toluenesulfonyl; 2) aromatic carbamate types such as benzyloxycarbonyl (cbz) and substituted benzyloxycarbonyls, 2-(p-biphenyl)-1-methylethoxycarbonyl, and 9-fluorenylmethyloxycarbonyl (Fmoc); 3) aliphatic carbamate types such as tert-butyloxycarbonyl (Boc), ethoxycarbonyl, diisopropylmethoxycarbonyl, and allyloxycarbonyl; 4) cyclic alkyl carbamate types such as cyclopentyloxycarbonyl and adamantyloxycarbonyl; 5) alkyl types such as triphenylmethyl and benzyl; 6) trialkylsilane such as trimethylsilane; and 7) thiol containing types such as phenylthiocarbonyl and dithiasuccinoyl.

Amine protecting groups may include, but are not limited to the following: 2,7-di-t-butyl-[9-(10,10-dioxo-10,10,10,10-tetratydrothio-xanthyl)]methyloxycarboneyl; 2-trimethylsilylethyloxycarbonyl; 2-phenylethyloxycarbonyl; 1,1-dimethyl-2,2-dibromoethyloxycarbonyl; 1-methyl-1-(4-biphenylyl)ethyloxycarbonyl; benzyloxycarbonyl, p-nitrobenzyloxycarbonyl; 2-(p-toluenesulfonyl) ethyloxycarbonyl; m-chloro-p-acyloxybenzyloxycarbonyl; 5-benzyisoxazolylmethyloxycrbonyl; p-(dihydroxyboryl) benzyloxycarbonyl; m-nitrophenyloxycarbonyl; o-nitrobenzyloxycarbonyl; 3,5-dimethoxybenzyloxycrbonyl; 3,4-dimethoxy-6-nitrobenzyloxycarbonyl; N'-p-toluenesulfonylaminocarbonyl; t-amyloxycarbonyl; p-decyloxybenzyloxycarbonyl; diisopropylmethyloxycarbonyl; 2,2-dimethoxycarbonylvinyloxycarbonyl; di(2-pyridyl)methyloxycarbonyl; 2-furanylmethyloxycarbonyl; phthalimide; dithiasuccinimide; 2,5-dimethylpyrrole; benzyl; 5-dibenzylsuberyl; triphenylmethyl; benzylidene; diphenylmethylene; and, methanesulfonamide.

By "reagent" is meant a compound of this invention capable of direct transformation into a metallopharmaceutical of this invention. Reagents may be utilized directly for the preparation of the metallopharmaceuticals of this invention or may be a component in a kit of this invention.

The term "binding agent" means a metallopharmaceutical of this invention having affinity for and capable of binding to the vitronectin receptor. The binding agents of this invention preferably have Ki<1000 nM.

Metallopharmaceutical as used herein is intended to refer to a pharmaceutically acceptable compound containing a metal, wherein the compound is useful for imaging, magnetic resonance imaging, contrast imaging, or x-ray imaging The metal is the cause of the imageable signal in diagnostic applications and the source of the cytotoxic radiation in radiotherapeutic applications. Radiopharmaceuticals are metallopharmaceuticals in which the metal is a radioisotope.

By "stable compound" or "stable structure" is meant herein a compound that is sufficiently robust to survive. isolation to a useful degree of purity from a reaction mixture, and formulation into an efficacious pharmaceutical agent.

The term 'substituted", as used herein, means that one or more hydrogens on the designated atom or group is replaced with a selection from the indicated group, provided that the designated atom's or group's normal valency is not exceeded, and that the substitution results in a stable compound. When a substituent is keto (i.e., =O), then 2 hydrogens on the atom are replaced.

The term "bond", as used herein, means either a single or double bond.

The term "salt", as used herein, is used as defined in the CRC Handbook of Chemistry and Physics, 65th Edition, CRC Press, Boca Raton, Fla. 1984, as any substance which yields ions, other than hydrogen or hydroxyl ions. As used herein, "pharmaceutically acceptable salts" refer to derivatives of the disclosed compounds modified by making acid or base salts. Examples of pharmaceutically acceptable salts include, but are not limited to, mineral or organic acid salts of basic residues such as amines; alkali or organic salts of acidic residues such as carboxylic acids; and the like.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences,* 17th ed., Mack Publishing Company, Easton, Pa., 1985, p. 1418, the disclosure of which is hereby incorporated by reference.

As used herein, "alkyl" is intended to include both branched and straight-chain saturated aliphatic hydrocarbon groups having the specified number of carbon atoms. $C_{1-10}$ alkyl, is intended to include $C_1$, $C_2$, $C_3$, $C_4$, $C_5$, $C_6$, $C_7$, $C_8$, $C_9$, and $C_{10}$ alkyl groups. Examples of alkyl include, but are not limited to, methyl, ethyl, n-propyl, i-propyl, n-butyl, s-butyl, t-butyl, n-pentyl, and s-pentyl. "Haloalkyl" is intended to include both branched and straight-chain saturated aliphatic hydrocarbon groups having the specified number of carbon atoms, substituted with 1 or more halogen (for example —$C_vF_w$ where v=1 to 3 and w=1 to (2v+1)). Examples of haloalkyl include, but are not limited to, trifluoromethyl, trichloromethyl, pentafluoroethyl, and pentachloroethyl. "Alkoxy" represents an alkyl group as defined above with the indicated number of carbon atoms attached through an oxygen bridge. $C_{1-10}$ alkoxy, is intended to include $C_1$, $C_2$, $C_3$, $C_4$, $C_5$, $C_6$, $C_7$, $C_8$, $C_9$, and $C_{10}$ alkoxy groups. Examples of alkoxy include, but are not limited to, methoxy, ethoxy, n-propoxy, i-propoxy, n-butoxy, s-butoxy, t-butoxy, n-pentoxy, and s-pentoxy. "Cycloalkyl" is intended to include saturated ring groups, such as cyclopropyl, cyclobutyl, or cyclopentyl. $C_{3-7}$ cycloalkyl, is intended to include $C_3$, $C_4$, $C_5$, $C_6$, and $C_7$ cycloalkyl groups Alkenyl" is intended to include hydrocarbon chains of either. a straight or branched configuration and one or more unsaturated carbon-carbon bonds which may occur in any. stable point along the chain, such as ethenyl and propenyl. $C_{2-10}$ alkenyl, is intended to include $C_2$, $C_3$, $C_4$, $C_5$, $C_6$, $C_7$, $C_5$, $C_9$, and $C_{10}$ alkenyl groups. "Alkynyl" is intended to include hydrocarbon chains of either a straight or branched configuration and one or more triple carbon-carbon bonds which may occur in any stable point along the chain, such as ethynyl and propynyl. $C_{2-10}$ alkynyl, is intended to include $C_2$, $C_3$, $C_4$, $C_5$, $C_6$, $C_7$, $C_5$, $C_9$, and $C_{10}$ alkynyl groups.

As used herein, "carbocycle" or "carbocyclic residue" is intended to mean any stable 3, 4, 5, 6, or 7-membered monocyclic or bicyclic or 7, 8, 9, 10, 11, 12, or 13-membered bicyclic or tricyclic, any of which may be saturated, partially unsaturated, or aromatic. Examples of such carbocycles include, but are not limited to, cyclopropyl, cyclobutyl, cyclopentyl, cyclohexyl, cycloheptyl, adamantyl, cyclooctyl, [3.3.0]bicyclooctane, [4.3.0]bicyclononane, [4.4.0]bicyclodecane, [2.2.2] bicyclooctane, fluorenyl, phenyl, naphthyl, indanyl, adamantyl, and tetrahydronaphthyl.

As used herein, the term "alkaryl" means an aryl group bearing an alkyl group of 1, 2, 3, 4, 5, 6, 7, 8, 9, or 10 carbon atoms; the term "aralkyl" means an alkyl group of 1, 2, 3, 4, 5, 6, 7, 8, 9, or 10 carbon atoms bearing an aryl group; the term "arylalkaryl" means an aryl group bearing an alkyl group of 1–10 carbon atoms bearing an aryl group; and the term "heterocycloalkyl" means an alkyl group of 1, 2, 3, 4, 5, 6, 7, 8, 9, or 10 carbon atoms bearing a heterocycle.

As used herein, the term "heterocycle" or "heterocyclic system" is intended to mean a stable 5, 6, or 7-membered monocyclic or bicyclic or 7, 8, 9, or 10-membered bicyclic heterocyclic ring which is saturated, partially unsaturated or unsaturated (aromatic), and which consists of carbon atoms and 1, 2, 3, or 4 heteroatoms independently selected; from the group consisting of N, NH, O and S and including any bicyclic group in which any of the above-defined heterocyclic rings is fused to a benzene ring. The nitrogen and sulfur heteroatoms may optionally be oxidized. The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. As used herein, the term "aromatic heterocyclic system" or "heteroaryl" is intended to mean a stable 5, 6, or 7-membered monocyclic or bicyclic or 7, 8, 9, or 10-membered bicyclic heterocyclic aromatic ring which consists of carbon atoms and 1, 2, 3, or 4 heterotams independently selected from the group consisting of N, NH, O and S. It is to be noted that total number of S and O atoms in the aromatic heterocycle is not more than 1.

Examples of heterocycles include, but are not limited to, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro [2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Preferred heterocycles include, but are not limited to, pyridinyl, furanyl, thienyl, pyrrolyl, pyrazolyl, pyrrolidinyl, imidazolyl, indolyl, benzimidazolyl, 1H-indazolyl, oxazolidinyl, benzotriazolyl, benzisoxazolyl, oxindolyl, benzoxazolinyl, and isatinoyl. Also included are fused ring and spiro compounds containing, for example, the above heterocycles.

A "polyalkylene glycol" is a polyethylene glycol, polypropylene glycol or polybutylene glycol having a molecular weight of less than about 5000, terminating in either a hydroxy or alkyl ether moiety.

A "carbohydrate" is a polyhydroxy aldehyde, ketone, alcohol or acid, or derivatives thereof, including polymers thereof having polymeric linkages of the acetal type.

A "cyclodextrin" is a cyclic oligosaccharide. Examples of cyclodextrins include, but are not limited to, α-cyclodextrin, hydroxyethyl-α-cyclodextrin, hydroxypropyl-α-cyclodextrin, β-cyclodextrin, hydroxypropyl-β-cyclodextrin, carboxymethyl-β-cyclodextrin, dihydroxypropyl-β-cyclodextrin, hydroxyethyl-β-cyclodextrin, 2,6 di-O-methyl-β-cyclodextrin, sulfated-β-cyclodextrin, γ-cyclodextrin, hydroxypropyl-γ-cyclodextrin, dihydroxypropyl-γ-cyclodextrin, hydroxyethyl-γ-cyclodextrin, and sulfated γ-cyclodextrin.

As used herein, the term "polycarboxyalkyl" means an alkyl group having between two and about 100 carbon atoms and a plurality of carboxyl substituents; and the term "polyazaalkyl" means a linear or branched alkyl group having between two and about 100 carbon atoms, interrupted by or substituted with a plurality of amine groups.

A "reducing agent" is a compound that reacts with a radionuclide, which is typically obtained as a relatively unreactive, high oxidation state compound, to lower its oxidation state by transferring electron(s) to the radionuclide, thereby making it more reactive. Reducing agents useful in the preparation of radiopharmaceuticals and in diagnostic kits useful for the preparation of said radiopharmaceuticals include but are not limited to stannous chloride, stannous fluoride, formamidine sulfinic acid, ascorbic acid, cysteine, phosphines, and cuprous or ferrous salts. Other reducing agents are described in Brodack et. al., PCT Application 94/22496, which is incorporated herein by reference.

A "transfer ligand" is a ligand that forms an intermediate complex with a metal ion that is stable enough to prevent unwanted side-reactions but labile enough to be converted to a metallopharmaceutical. The formation of the intermediate complex is kinetically favored while the formation of the metallopharmaceutical is thermodynamically favored. Transfer ligands useful in the preparation of metallopharmaceuticals and in diagnostic kits useful for the preparation of diagnostic radiopharmaceuticals include but are not limited to gluconate, glucoheptonate, mannitol, glucarate, N,N,N',N'-ethylenediaminetetraacetic acid, pyrophosphate and methylenediphosphonate. In general, transfer ligands are comprised of oxygen or nitrogen donor. atoms.

The term "donor atom" refers to the atom directly attached to a metal by a chemical bond.

"Ancillary" or "co-ligands" are ligands that are incorporated into a radiopharmaceutical during its synthesis. They serve to complete the coordination sphere of the radionuclide together with the chelator or radionuclide bonding unit of the reagent. For radiopharmaceuticals comprised of a binary ligand system, the radionuclide coordination sphere is composed of one or more chelators or bonding units from one or more reagents and one or more ancillary or co-ligands, provided that there are a total of two types of ligands, chelators or bonding units. For example, a radiopharmaceutical comprised of one chelator or bonding unit from one reagent and two of the same ancillary or co-ligands and a radiopharmaceutical comprised of two chelators or bonding units from one or two reagents and one ancillary or co-ligand are both considered to be comprised of-binary ligand systems. For radiopharmaceuticals comprised of a ternary ligand system, the radionuclide coordination sphere is composed of one or more chelators or bonding units from one or more reagents and one or more of two different types of ancillary or co-ligands, provided that there are a total of three types of ligands, chelators or bonding units. For example, a radiopharmaceutical comprised of one chelator or bonding unit from one reagent and two different ancillary or co-ligands is considered to be comprised of a ternary ligand system.

Ancillary or co-ligands useful in the preparation of radiopharmaceuticals and in diagnostic kits useful for the preparation of said radiopharmaceuticals are comprised of one or more oxygen, nitrogen, carbon, sulfur, phosphorus, arsenic, selenium, and tellurium donor atoms. A ligand can be a transfer ligand in the synthesis of a radiopharmaceutical and also serve as an ancillary or co-ligand in another radiopharmaceutical. Whether a ligand is termed a transfer or ancillary or co-ligand depends on whether the ligand remains in the radionuclide coordination sphere in the radiopharmaceutical, which is determined by the coordination chemistry of the radionuclide and the chelator or bonding unit of the reagent or reagents.

A "chelator" or "bonding unit" is the moiety or group on a reagent that binds to a metal ion through the formation of chemical bonds with one or more donor atoms.

The term "binding site" means the site in vivo or in vitro that binds a biologically active molecule.

A "diagnostic kit" or "kit" comprises a collection of components, termed the formulation, in one or more vials which are used by the practicing end user in a clinical or pharmacy setting to synthesize diagnostic radiopharmaceuticals. The kit provides all the requisite components to synthesize and use the diagnostic radiopharmaceutical except those that are commonly available to the practicing end user, such as water or saline for injection, a solution of the radionuclide, equipment for heating the kit during the synthesis of the radiopharmaceutical, if required, equipment necessary for administering the radiopharmaceutical to the patient such as syringes and shielding, and imaging equipment.

Therapeutic radiopharmaceuticals, X-ray contrast agent pharmaceuticals, ultrasound contrast agent pharmaceuticals and metallopharmaceuticals for magnetic resonance imaging contrast are provided to the end user in their-final form in a formulation contained typically in one vial, as either a lyophilized solid or an aqueous solution. The end user reconstitutes the lyophilized with water or saline and withdraws the patient dose or just withdraws the dose from the aqueous solution formulation as provided.

A "lyophilization aid" is a component that has favorable physical properties for lyophilization, such as the glass transition temperature, and is added to the formulation to improve the physical properties of the combination of all the components of the formulation for lyophilization.

A "stabilization aid" is a component that is added to the metallopharmaceutical or to the diagnostic kit either to stabilize the metallopharmaceutical or to prolong the shelf-life of the kit before it must be used. Stabilization aids can be antioxidants, reducing agents or radical scavengers and can provide improved stability by reacting preferentially with species that degrade other components or the metallopharmaceutical.

A "solubilization aid" is a component that improves the solubility of one or more other components in the medium required for the formulation.

A "bacteriostat" is a component that inhibits the growth of bacteria in a formulation either during its storage before use of after a diagnostic kit is used to, synthesize a radiopharmaceutical The term "amino acid" as used herein means an organic compound containing both a basic amino group and an acidic carboxyl group. Included within this term are natural amino acids (e.g., L-amino acids), modified and unusual amino acids (e.g., D-amino acids), as well as amino acids which are known to occur biologically in free or combined form but usually do not occur in proteins. Included within this term are modified and unusual amino acids, such as those disclosed in, for example, Roberts and Vellaccio (1983) *The Peptides,* 5: 342–429, the teaching of which is hereby incorporated by reference. Natural protein occurring amino acids include, but are not limited to, alanine, arginine, asparagine, aspartic acid, cysteine, glutamic acid, glutamine, glycine, histidine, isoleucine, leucine, lysine, methionine, phenylalanine, serine, threonine, tyrosine, tyrosine, tryptophan, proline, and valine. Natural non-protein amino acids include, but are not limited to arginosuccinic acid, citrulline, cysteine sulfinic acid, 3,4-dihydroxyphenylalanine, homocysteine, homoserine, ornithine, 3-monoiodotyrosine, 3,5-diiodotryosine, 3,5,5'-triiodothyronine, and 3,3',5,5'-tetraiodothyronine. Modified or unusual amino acids which can be used to practice the invention include, but are not limited to, D-amino acids, hydroxylysine, 4-hydroxyproline, an N—Cbz-protected amino acid, 2,4-diaminobutyric acid, homoarginine, norleucine, N-methylaminobutyric acid, naphthylalanine, phenylglycine, β-phenylproline, tert-leucine, 4-aminocyclohexylalanine, N-methyl-norleucine, 3,4-dehydroproline, N,N-dimethylaminoglycine, N-methylaminoglycine, 4-aminopiperidine-4-carboxylic acid, 6-aminocaproic acid, trans-4-(aminomethyl)-cyclohexanecarboxylic acid, 2-, 3-, and 4-(aminomethyl)-benzoic acid, 1-aminocyclopentanecarboxylic acid, 1-aminocyclopropanecarboxylic acid, and 2-benzyl-5-aminopentanoic acid.

The term "peptide" as used herein means a linear compound that consists of two or more amino acids (as defined herein) that are linked by means of a peptide bond. A "peptide" as used in the presently claimed invention is intended to refer to a moiety with a molecular weight of less than 10,000 Daltons, preferable less than 5,000 Daltons, and more preferably less than 2,500 Daltons. The term "peptide" also includes compounds containing both peptide and non-peptide components, such as pseudopeptide or peptidomimetic residues or other non-amino acid components. Such a compound containing both peptide and non-peptide components may also be referred to as a "peptide analog".

A "pseudopeptide" or "peptidomimetic" is a compound which mimics the structure of an amino acid residue or a peptide, for example, by using linking groups other than amide linkages between the peptide mimetic and an amino acid residue (pseudopeptide bonds) and/or by using non-amino acid substituents and/or a modified amino acid residue. A "pseudopeptide residue" means that portion of an pseudopeptide or peptidomimetic that is present in a peptide.

The term "peptide bond" means a covalent amide linkage formed by loss of a molecule of water between the carboxyl group of one amino acid and the amino group of a second amino acid.

The term "pseudopeptide bonds" includes peptide bond isosteres which may be used in place of or as substitutes for the normal amide linkage. These substitute or amide "equivalent" linkages are formed from combinations of atoms not normally found in peptides or proteins which mimic the spatial requirements of the amide bond and which should stabilize the molecule to enzymatic degradation.

| | |
|---|---|
| Acm | acetamidomethyl |
| b-Ala, beta-Ala or bAla | 3-aminopropionic acid |
| ATA | 2-aminothiazole-5-acetic acid or 2-aminothiazole--5-acetyl group |
| Boc | t-butyloxycarbonyl |
| CBZ, Cbz or Z | Carbobenzyloxy |
| Cit | citrulline |
| Dap | 2,3-diaminopropionic acid |
| DCC | dicyclohexylcarbodiimide |
| DIEA | diisopropylethylamine |
| DMAP | 4-dimethylaminopyridine |
| EOE | ethoxyethyl |
| HBTU | 2-(1H-Benzotriazol-1-yl)-1,1,3,3-tetramethyluronium hexafluorophosphate |

-continued

| | |
|---|---|
| hynic | boc-hydrazinonicotinyl group or 2-[[[5-,[carbonyl]-2-pyridinyl]hydrazono]methyl]-benzenesulfonic acid, |
| Mbs | 4-methoxybenzenesulfonyl |
| Mtr | 4-methoxy-2,3,6-trimethylbenzenesulfonyl |
| Mts | mesitylene-2-sulfonyl |
| NMeArg or MeArg | a-N-methyl arginine |
| NMeAsp | a-N-methyl aspartic acid |
| NMM | N-methylmorpholine |
| OcHex | O-cyclohexyl |
| OBt | O-benzotriazolyl |
| OBzl | O-benzyl |
| ONp | O-4-nitrophenyl |
| OPfp | O-pentafluorophenyl |
| oSu | O-succinimidyl |
| Pbf | 2,2,4,6,7-pentamethyldihydrobenzofuran-5-sulfonyl |
| Pmc | 2,2,5,7,8-pentamethylchroman-6-sulfonyl |
| TBTU | 2-(1H-Benzotriazol-1-yl)-1,1,3,3-tetramethyluronium tetrafluoroborate |
| THF | tetrahydrofuranyl |
| THP | tetrahydropyranyl |
| Tos | tosyl |
| Tr | trityl |

The following conventional three-letter amino acid abbreviations are used herein; the conventional one-letter amino acid abbreviations are NOT used herein:

Ala=alanine
Arg=arginine
Asn=asparagine
Asp=aspartic acid
Cys=cysteine
Gln=glutamine
Glu=glutamic acid
Gly=glycine
His=histidine
Ile=isoleucine
Leu=leucine
Lys=lysine
Met=methionine
Nle=norleucine
Orn=ornithine
Phe=phenylalanine
Phg=phenylglycine
Pro=proline
Sar=sarcosine
Ser=serine
Thr=threonine
Trp=tryptophan
Tyr=tyrosine
Val=valine The targeting moieties of the present invention, preferably, have a binding affinity for their respective target of less than 1000 nM. More preferably, the targeting moieties of the present invention, preferably, have a binding affinity of less than 100 nM. Even more preferably, the targeting moieties of the present invention, preferably, have a binding affinity of less than 10 nM.

$S_f$ as used herein is a surfactant that is either a lipid or a compound of the formula $A^1$-E-$A^2$, defined above. The surfactant is intended to form a vesicle (e.g., a microsphere) capable of containing an echogenic gas. The ultrasound contrast agent compositions of the present invention are intended to be capable upon agitation (e.g., shaking, stirring, etc.) of encapsulating an echogenic gas in a vescicle in such a way as to allow for the resultant product to be useful as an ultrasound contrast agent.

"Vesicle" refers to a spherical entity that is characterized by the presence of an internal void. Preferred vesicles are formulated from lipids, including the various lipids described herein. In any given vesicle, the lipids may be in the form of a monolayer or bilayer, and the mono- or bilayer lipids may be used to form one of more mono- or bilayers. In the case of more than one mono- or bilayer, the mono- or bilayers are generally concentric. The lipid vesicles described herein include such entities commonly referred to as liposomes, micelles, bubbles, microbubbles, microspheres and the like. Thus, the lipids may be used to form a unilamellar vesicle (comprised of one monolayer or bilayer), an oligolamellar vesicle (comprised of about two or about three monolayers or bilayers) or a multilamellar vesicle (comprised of more than about three monolayers or bilayers). The internal void of the vesicles may be filled with a liquid, including, for example, an aqueous liquid, a gas, a gaseous precursor, and/or a solid or solute material, including, for example, a bioactive agent, as desired.

"Vesicular composition" refers to a composition which is formulate from lipids and which comprises vesicles.

"Vesicle formulation" refers to a composition which comprises vesicles and a bioactive agent.

Microsphere, as used herein, is preferably a sphere of less than or equal to 10 microns. Liposome, as used herein, may include a single lipid layer (a lipid monolayer), two lipid layers (a lipid bilayer) or more than two lipid layers (a lipid multilayer). "Lipsomes" refers to a generally spherical cluster or aggregate of amphipathic compounds, including lipid compounds, typically in the form of one or more concentric layers, for example, bilayers. They may also be referred to herein as lipid vesicles.

The term "bubbles", as used herein, refers to vesicles which are generally characterized by the presence of one or more membranes or walls surrounding an internal void that is filled with a gas or precursor thereto. Exemplary bubbles include, for example, liposomes, micelles and the like.

"Lipid" refers to a synthetic or naturally-occurring amphipathic compound which comprises a hydrophilic component and a hydrophobic component. Lipids include, for example, fatty acids, neutral fats, phosphatides, glycolipids, aliphatic alchols and waxes, terpenes and steroids.

"Lipid composition" refers to a composition that comprises a lipid compound. Exemplary lipid compositions include suspensions, emulsions and vesicular compositions.

"Lipid formulation" refers to a composition that comprises a lipid compound and a bioactive agent.

Examples of classes of suitable lipids and specific suitable lipids include: phosphatidylcholines, such as dioleoylphosphatidylcholine, dimyristoylphosphatidylcholine, dipalmitoylphosphatidylcholine (DPPC), and distearoylphosphatidylcholine; phosphatidylethanolamines, such as dipalmitoylphosphatidylethanolamine (DPPE), dioleoylphosphatidylethanolamine and N-succinyl-dioleoylphosphatidylethanolamine; phosphatidylserines; phosphatidylglycerols; sphingolipids; glycolipids, such as ganglioside GM1; glucolipids; sulfatides; glycosphingolipids; phosphatidic acids, such as dipalmatoylphosphatidic acid (DPPA); palmitic fatty acids; stearic fatty acids; arachidonic fatty acids; lauric fatty acids; myristic fatty acids; lauroleic fatty acids; physeteric fatty acids; myristoleic fatty acids; palmitoleic fatty acids; petroselinic fatty acids; oleic fatty acids; isolauric fatty acids; isomyristic fatty acids; isopalmitic fatty acids; isostearic fatty acids; cholesterol and cholesterol derivatives, such as cholesterol hemisuccinate, cholesterol sulfate, and cholesteryl-(4'-trimethylammonio)-butanoate; polyoxyethylene fatty acid esters; polyoxyethylene fatty acid alcohols; polyoxyethylene fatty acid alcohol ethers; polyoxyethylated sorbitan fatty acid esters; glycerol polyethylene glycol oxystearate; glycerol polyethylene glycol ricinoleate; ethoxylated soybean sterols; ethoxylated castor oil; polyoxyethylene-polyoxypropylene fatty acid polymers; polyoxyethylene fatty acid stearates; 12-(((7'-diethylaminocoumarin-3-yl)-carbonyl)-methylamino)-octadecanoic acid; N-[12-(((7'-diethylamino-coumarin-3-yl)-carbonyl)-methylamino)octadecanoyl]-2-amino-palmitic acid; 1,2-dioleoyl-sn-glycerol; 1,2-dipalmitoyl-sn-3-succinylglycerol; 1,3-dipalmitoyl-2-succinyl-glycerol; and 1-hexadecyl-2-palmitoyl-glycerophosphoethanolamine and palmitoylhomocysteine; lauryltrimethylammonium bromide; cetyltrimethylammonium bromide; myristyltrimethylammonium bromide; alkyldimethylbenzylammonium chlorides,such as wherein alkyl is a $C_{12}$, $C_{14}$ or $C_{16}$ alkyl; benzyldimethyldodecylammonium bromide; benzyldimethyldodecylammonium chloride, benzyldimethylhexadecylammonium bromide; benzyldimethylhexadecylammonium chloride; benzyldimethyltetradecylammonium bromide; benzyldimethyltetradecylammonium chloride; cetyldimethylethylammonium bromide; cetyldimethylethylammonium chloride; cetylpyridinium bromide; cetylpyridinium chloride; N-[1,2,3-dioleoyloxy)propyl]-N,N,N-trimethylammonium chloride (DOTMA); 1,2-dioleoyloxy-3-(trimethylammonio)propane (DOTAP); and 1,2-dioleoyl-c-(4'-trimethylammonio)-butanoyl-sn-glycerol (DOTB).

The echogenic gas may be one gas or mixture of gases, such as $CF_4$, $C_2F_6$, $C_3F_8$, cyclo-$C_4F_8$, $C_4F_{10}$, $C_5F_{12}$, cyclo-$C_5F_{10}$, cyclo-$C_4F_7$ (1-trifluoromethyl), propane (2-trifluoromethyl)-1,1,1,3,3,3 hexafluoro, and butane (2-trifluoromethyl)-1,1,1,3,3,3,4,4,4 nonafluoro. Also preferred are the the corresponding unsaturated versions of the above compounds, for example $C_2F_4$, $C_3F_6$, the isomers of $C_4F_8$. Also, mixtures of these gases, especially mixtures of perfluorocarbons with other perfluorocarbons and mixtures of perfluorocarbons with other inert gases, such as air, $N_2$, $O_2$, He, would be useful. Examples of these can be found in Quay, U.S. Pat. No. 5,595,723, the contents of which are herein incorporated by reference.

X-ray contrast agents of the present invention are comprised of one or more angiogenic tumor vasculature targeting moieties attached to one or more X-ray absorbing or "heavy" atoms of atomic number 20 or greater, further comprising an optional linking moiety, $L_n$, between the targeting moieties and the x-ray absorbing atoms. The frequently used heavy atom in X-ray contrast agents is iodine. Recently, X-ray contrast agents comprised of metal chelates (Wallace, R., U.S. Pat. No. 5,417,959) and polychelates comprised of a plurality of metal ions (Love, D., U.S. Pat. No. 5,679,810) have been disclosed. More recently, multinuclear cluster complexes have been disclosed as X-ray contrast agents (U.S. Pat. No. 5,804,161, PCT WO91/14460, and PCT WO 92/17215). Examples of X-ray agents include the non-radioactive or naturally occurring analogs of the above listed radionuclides (e.g., Re, Sm, Ho, Lu, Pm, Y, Bi, Pd, Gd, La, Au, Au, Yb, Dy, Cu, Rh, Ag, and Ir).

MRI contrast agents of the present invention are comprised of one or more angiogenic tumor vasculature targeting moieties attached to one or more paramagnetic metal ions, further comprising an optional linking moiety, $L_n$, between the targeting moieties and the paramagnetic metal ions. The paramagnetic metal ions are present in the form of metal complexes or metal oxide particles. U.S. Pat. Nos. 5,412,148 and 5,760,191 describe examples of chelators for paramagnetic metal ions for use in MRI contrast agents. U.S. Pat. Nos. 5,801,228, 5,567,411, and 5,281,704 describe examples of polychelants useful for complexing more than one paramagnetic metal ion for use in MRI contrast agents. U.S. Pat. No. 5,520,904 describes particulate compositions comprised of paramagnetic metal ions for use as MRI contrast agents.

The pharmaceuticals of the present invention can be synthesized by several approaches. One approach involves the synthesis of the targeting peptide or peptidomimetic moiety, Q, and direct attachment of one or more moieties, Q to one or more metal chelators or bonding moieties, $C_h$, or to a paramagnetic metal ion or heavy atom containing solid particle, or to an echogenic gas microbubble. Another approach involves the attachment of one or more moieties, Q to the linking group, $L_n$, which is then attached to one or more metal chelators or bonding moieties, $C_h$, or to a paramagnetic metal ion or heavy atom containing solid particle, or to an echogenic gas microbubble. Another approach, useful in the synthesis of pharmaceuticals wherein d is 1, involves the synthesis of the moiety, Q—$L_n$, together, by incorporating an amino acid or amino acid mimetic residue bearing $L_n$ into the synthesis of the peptide or peptidomimetic. The resulting moiety, Q—$L_n$, is then attached to one or more metal chelators or bonding moieties, $C_h$, or to a paramagnetic metal ion or heavy atom containing solid particle, or to an echogenic gas microbubble. Another approach involves the synthesis of a peptide or peptidomimetic, Q, bearing a fragment of the linking group, $L_n$, one or more of which are then attached to the remainder of the linking group and then to one or more metal chelators or bonding moieties, $C_h$, or to a paramagnetic metal ion or heavy atom containing solid particle, or to an echogenic gas microbubble.

The peptides or peptidomimetics, Q, optionally bearing a linking group, $L_n$, or a fragment of the linking group, can be synthesized using standard synthetic methods known to those skilled in the art. Preferred methods include but are not limited to those methods described below.

Generally, peptides and peptidomimetics are elongated by deprotecting the alpha-amine of the C-terminal residue and coupling the next suitably protected amino acid through a peptide linkage using the methods described. This deprotection and coupling procedure is repeated until the desired sequence is obtained. This coupling can be performed with the constituent amino acids in a stepwise fashion, or condensation of fragments (two to several amino acids), or combination of both processes, or by solid phase peptide synthesis according to the method originally described by Merrifield, J. Am. Chem. Soc., 85, 2149–2154 (1963), the disclosure of which is hereby incorporated by reference.

The peptides and peptidomimetics may also be synthesized using automated synthesizing equipment. In addition to the foregoing, procedures for peptide and peptidomimetic synthesis are described in Stewart and Young, "Solid Phase Peptide Synthesis", 2nd ed, Pierce Chemical Co., Rockford, Ill. (1984); Gross, Meienhofer, Udenfriend, Eds., "The Peptides: Analysis, Synthesis, Biology, Vol. 1, 2, 3, 5, and 9, Academic Press, New York, (1980–1987); Bodanszky, "Peptide Chemistry: A Practical Textbook", Springer-Verlag, New York (1988); and Bodanszky et al. "The Practice of Peptide Synthesis" Springer-Verlag, New York (1984), the disclosures of which are hereby incorporated by reference.

The coupling between two amino acid derivatives, an amino acid and a peptide or peptidomimetic, two peptide or peptidomimetic fragments, or the cyclization of a peptide or peptidomimetic can be carried out using standard coupling procedures such as the azide method, mixed carbonic acid anhydride (isobutyl chloroformate) method, carbodiimide (dicyclohexylcarbodiimide, diisopropylcarbodiimide, or water-soluble carbodiimides) method, active ester (p-nitrophenyl ester, N-hydroxysuccinic imido ester) method, Woodward reagent K method, carbonyldiimidazole method, phosphorus reagents such as BOP-Cl, or oxidation-reduction method. Some of these methods (especially the carbodiimide) can be enhanced by the addition of 1-hydroxybenzotriazole. These coupling reactions may be performed in either solution (liquid phase) or solid phase.

The functional groups of the constituent amino acids or amino acid mimetics must be protected during the coupling reactions to avoid undesired bonds being formed. The protecting groups that can be used are listed in Greene, "Protective Groups in Organic Synthesis" John Wiley & Sons, New York (1981) and "The Peptides: Analysis, Synthesis, Biology, Vol., 3, Academic Press, New York (1981), the disclosure of which is hereby incorporated by reference.

The alpha-carboxyl group of the C-terminal residue is usually protected by an ester that can be cleaved to give the carboxylic acid. These protecting groups include: 1) alkyl esters such as methyl and t-butyl, 2) aryl esters such as benzyl and substituted benzyl, or 3) esters which can be cleaved by mild base treatment or mild reductive means such as trichloroethyl and phenacyl esters. In the solid phase case, the C-terminal amino acid is attached to an insoluble carrier (usually polystyrene). These insoluble carriers contain a group which will react with the carboxyl group to form a bond which is stable to the elongation conditions but readily cleaved later. Examples of which are: oxime resin (DeGrado and Kaiser (1980) *J. Org. Chem.* 45, 1295–1300) chloro or bromomethyl resin, hydroxymethyl resin, and aminomethyl resin. Many of these resins are commercially available with the desired C-terminal amino acid already incorporated.

The alpha-amino group of each amino acid must be protected. Any protecting group known in the art can be used. Examples of these are: 1) acyl types such as formyl, trifluoroacetyl, phthalyl, and p-toluenesulfonyl; 2) aromatic carbamate types such as benzyloxycarbonyl (Cbz) and substituted benzyloxycarbonyls, 1-(p-biphenyl)-1-methylethoxycarbonyl, and 9-fluorenylmethyloxycarbonyl (Fmoc); 3) aliphatic carbamate types such as tert-butyloxycarbonyl (Boc), ethoxycarbonyl, diisopropylmethoxycarbonyl, and allyloxycarbonyl; 4) cyclic alkyl carbamate types such as cyclopentyloxycarbonyl and adamantyloxycarbonyl; 5) alkyl types such as triphenylmethyl and benzyl; 6) trialkylsilane such as trimethylsilane; and 7) thiol containing types such as phenylthiocarbonyl and dithiasuccinoyl. The preferred alpha-amino protecting group is either Boc or Fmoc. Many amino acid or amino acid mimetic derivatives suitably protected for peptide synthesis are commercially available.

The alpha-amino protecting group is cleaved prior to the coupling of the next amino acid. When the Boc-group is used, the methods of choice are trifluoroacetic acid, neat or in dichloromethane, or HCl in dioxane. The resulting ammonium salt is then neutralized either prior to the coupling or in situ with basic solutions such as aqueous buffers, or tertiary amines in dichloromethane or dimethylformamide. When the Fmoc group is used, the reagents of choice are piperidine or substituted piperidines in dimethylformamide, but any secondary amine or aqueous basic solutions can be used. The deprotection is carried out at a temperature between 0° C. and room temperature.

Any of the amino acids or amino acid mimetics bearing side chain functionalities must be protected during the preparation of the peptide using any of the above-identified groups. Those skilled in the art will appreciate that the selection and use of appropriate protecting groups for these side chain functionalities will depend upon the amino acid or amino acid mimetic and presence of other protecting groups in the peptide or peptidomimetic. The selection of such a protecting group is important in that it must not be removed during the deprotection and coupling of the alpha-amino group.

For example, when Boc is chosen for the alpha-amine protection the following protecting groups are acceptable: p-toluenesulfonyl (tosyl) moieties and nitro for arginine; benzyloxycarbonyl, substituted benzyloxycarbonyls, tosyl or trifluoroacetyl for lysine; benzyl or alkyl esters such as cyclopentyl for glutamic and aspartic acids; benzyl ethers for serine and threonine; benzyl ethers, substituted benzyl ethers or 2-bromobenzyloxycarbonyl for tyrosine; p-methylbenzyl, p-methoxybenzyl, acetamidomethyl, benzyl, or t-butylsulfonyl for cysteine; and the indole of tryptophan can either be left unprotected or protected with a formyl group.

When Fmoc is chosen for the alpha-amine protection usually tert-butyl based protecting groups are acceptable. For instance, Boc can be used for lysine, tert-butyl ether for serine, threonine and tyrosine, and tert-butyl ester for glutamic and aspartic acids.

Once the elongation of the peptide or peptidomimetic, or the elongation and cyclization of a cyclic peptide or peptidomimetic is completed all of the protecting groups are removed. For the liquid phase synthesis the protecting groups are removed in whatever manner as dictated by the choice of protecting groups. These procedures are well known to those skilled in the art.

When a solid phase synthesis is used to synthesize a cyclic peptide or peptidomimetic, the peptide or peptidomimetic should be removed from the resin without simultaneously removing protecting groups from functional groups that might interfere with the cyclization process. Thus, if the peptide or peptidomimetic is to be cyclized in solution, the cleavage conditions need to be chosen such that a free a-carboxylate and a free a-amino group are generated without simultaneously removing other protecting groups. Alternatively, the peptide or peptidomimetic may be removed from the resin by hydrazinolysis, and then coupled by the azide method. Another very convenient method involves the synthesis of peptides or peptidomimetics on an oxime resin, followed by intramolecular nucleophilic displacement from the resin, which generates a cyclic peptide or peptidomimetic (Osapay, Profit, and Taylor (1990) *Tetrahedron Letters* 43, 6121–6124). When the oxime resin is employed, the Boc protection scheme is generally chosen. Then, the preferred method for removing side chain protecting groups generally involves treatment with anhydrous HF containing additives such as dimethyl sulfide, anisole, thioanisole, or p-cresol at 0° C. The cleavage of the peptide or peptidomimetic can also be accomplished by other acid reagents such as trifluoromethanesulfonic acid/trifluoroacetic acid mixtures.

Unusual amino acids used in this invention can be synthesized by standard methods familiar to those skilled in the art ("The Peptides: Analysis, Synthesis, Biology, Vol. 5, pp. 342–449, Academic Press, New York (1981)). N-Alkyl amino acids can be prepared using procedures described in previously (Cheung et al., (1977) *Can. T. Chem.* 55, 906; Freidinger et al., (1982) *J. Org. Chem.* 48, 77 (1982)), which are incorporated herein by reference.

Additional synthetic procedures that can be used by one of skill in the art to synthesize the peptides and peptidomimetics targeting moieties are described in PCT WO94/22910, the contents of which are herein incorporated by reference.

The attachment of linking groups, $L_n$, to the peptides and peptidomimetics, Q; chelators or bonding units, $C_h$, to the peptides and peptidomimetics, Q, or to the linking groups, $L_n$; and peptides and peptidomimetics bearing a fragment of the linking group to the remainder of the linking group, in combination forming the moiety, $(Q)_d$—$L_n$, and then to the moiety $C_h$; can all be performed by standard techniques. These include, but are not limited to, amidation, esterification, alkylation, and the formation of ureas or thioureas. Procedures for performing these attachments can be found in Brinkley, M., *Bioconjugate Chemistry* 1992, 3(1), which is incorporated herein by reference.

A number of methods can be used to attach the peptides and peptidomimetics, Q, to paramagnetic metal ion or heavy atom containing solid particles, $X^2$, by one of skill in the art of the surface modification of solid particles. In general, the targeting moiety Q or the combination $(Q)_d L_n$ is attached to a coupling group that react with a constituent of the surface of the solid particle. The coupling groups can be any of a number of silanes which react with surface hydroxyl groups on the solid particle surface, as described in co-pending U.S. application Ser. No. 60/092,360, and can also include polyphosphonates, polycarboxylates, polyphosphates or mixtures thereof which couple with the surface of the solid particles, as described in U.S. Pat. No. 5,520,904.

A number of reaction schemes can be used to attach the peptides and peptidomimetics, Q, to the surfactant microsphere, $X^3$. These are illustrated in following reaction schemes where $S_f$ represents a surfactant moiety that forms the surfactant microsphere.

Acylation Reaction:

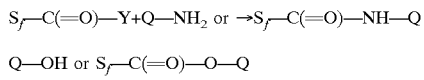

Y is a leaving group or active ester

Disulfide Coupling:

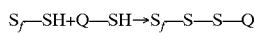

Sulfonamide Coupling:

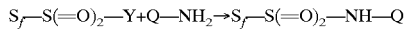

Reductive Amidation:

In these reaction schemes, the substituents $S_f$ and Q can be reversed as well.

The linking group $L_n$ can serve several roles. First it provides a spacing group between the metal chelator or bonding moiety, $C_h$, the paramagnetic metal ion or heavy atom containing solid particle, $X^2$, and the surfactant microsphere, $X^3$, and the one or more of the peptides or peptidomimetics, Q, so as to minimize the possibility that the moieties C—X, $C_h$—$X^1$, $X^2$, and $X^3$, will interfere with the interaction of the recognition sequences of Q with angiogenic tumor vasculature receptors. The necessity of incorporating a linking group in a reagent is dependent on the identity of Q, $C_h$—X, $C_h$—$X^1$, $X^2$, and $X^3$. If $C_h$—X, $C_h$—$X^1$, $X^2$, and $X^3$, cannot be attached to Q without substantially diminishing its affinity for the receptors, then a linking group is used. A linking group also provides a means of independently attaching multiple peptides and peptidomimetics, Q, to one group that is attached to $C_h$—X, $C_h$—$X^1$, $X^2$, or $X^3$.

The linking group also provides a means of incorporating a pharmacokinetic modifier into the pharmaceuticals of the present invention. The pharmacokinetic modifier serves to direct the biodistibution of the injected pharmaceutical other than by the interaction of the targeting moieties, Q, with the receptors expressed in the tumor neovasculature. A wide variety of functional groups can serve as pharmacokinetic modifiers, including, but not limited to, carbohydrates, polyalkylene glycols, peptides or other polyamino acids, and cyclodextrins. The modifiers can be used to enhance or decrease hydrophilicity and to enhance or decrease the rate of blood clearance. The modifiers can also be used to direct the route of elimination of the pharmaceuticals. Preferred pharmacokinetic modifiers are those that result in moderate to fast blood clearance and enhanced renal excretion.

The metal chelator or bonding moiety, $C_h$, is selected to form stable complexes with the metal ion chosen for the particular application. Chelators or bonding moieties for diagnostic radiopharmaceuticals are selected to form stable complexes with the radioisotopes that have imageable gamma ray or positron emissions, such as $^{99m}$Tc, $^{95}$Tc, $^{111}$In, $^{62}$Cu, $^{60}$Cu, $^{64}$Cu, $^{67}$Ga, $^{68}$Ga, 86Y.

Chelators for technetium, copper and gallium isotopes are selected from diaminedithiols, monoaminemonoamidedithiols, triamide-monothiols, monoaminediamide-monothiols, diaminedioximes, and hydrazines. The chelators are generally tetradentate with donor atoms selected from nitrogen, oxygen and sulfur. Preferred reagents are comprised of chelators having amine nitrogen and thiol sulfur donor atoms and hydrazine bonding units. The thiol sulfur atoms and the hydrazines may bear a protecting group which can be displaced either prior to using the reagent to synthesize a radiopharmaceutical or preferably in situ during the synthesis of the radiopharmaceutical.

Exemplary thiol protecting groups include those listed in Greene and Wuts, "Protective Groups in Organic Synthesis" John Wiley & Sons, New York (1991), the disclosure of which is hereby incorporated by reference. Any thiol protecting group known in the art can be used. Examples of thiol protecting groups include, but are not limited to, the following: acetamidomethyl, benzamidomethyl, 1-ethoxyethyl, benzoyl, and triphenylmethyl.

Exemplary protecting groups for hydrazine bonding units are hydrazones which can be aldehyde or ketone hydrazones having substituents selected from hydrogen, alkyl, aryl and heterocycle. Particularly preferred hydrazones are described in co-pending U.S. Ser. No. 08/476,296 the disclosure of which is herein incorporated by reference in its entirety.

The hydrazine bonding unit when bound to a metal radionuclide is termed a hydrazido, or diazenido group and serves as the point of attachment of the radionuclide to the remainder of the radiopharmaceutical. A diazenido group can be either terminal (only one atom of the group is bound to the radionuclide) or chelating. In order to have a chelating diazenido group at least one other atom of the group must also be bound to the radionuclide. The atoms bound to the metal are termed donor atoms.

Chelators for $^{111}$In and 86Y are preferably selected from cyclic and acyclic polyaminocarboxylates such as DTPA, DOTA, DO3A, 2-benzyl-DOTA, alpha-(2-phenethyl)1,4,7, 10-tetraazacyclododecane-1-acetic-4,7,10-tris (methylacetic)acid, 2-benzyl-cyclohexyldiethylenetriaminepentaacetic acid, 2-benzyl-6-methyl-DTPA, and 6,6"-bis[N,N,N",N"-tetra(carboxymethyl)aminomethyl)-4'-(3-amino-4-methoxyphenyl)-2,2':6',2"-terpyridine. Procedures for synthesizing these chelators that are not commercially available can be found in Brechbiel, M. and Gansow, O., *J. Chem. Soc. Perkin Trans.* 1992, 1, 1175; Brechbiel, M. and Gansow, O., *Bioconjugate Chem.* 1991, 2, 187; Deshpande, S., et. al., *J. Nucl. Med.* 1990, 31, 473; Kruper, J., U.S. Pat. No. 5,064,956, and Toner, J., U.S. Pat. No. 4,859,777, the disclosures of which are hereby incorporated by reference in their entirety.

The coordination sphere of metal ion includes all the ligands or groups bound to the metal. For a transition metal radionuclide to be stable it typically has a coordination number (number of donor atoms) comprised of an integer greater than or equal to 4 and less than or equal to 8; that is there are 4 to 8 atoms bound to the metal and it is said to have a complete coordination sphere. The requisite coordination number for a stable radionuclide complex is determined by the identity of the radionuclide, its oxidation state, and the type of donor atoms. If the chelator or bonding unit does not provide all of the atoms necessary to stabilize the metal radionuclide by completing its coordination sphere, the coordination sphere is completed by donor atoms from other ligands, termed ancillary or co-ligands, which can also be either terminal or chelating.

A large number of ligands can serve as ancillary or co-ligands, the choice of which is determined by a variety of considerations such as the ease of synthesis of the radiopharmaceutical, the chemical and physical properties of the ancillary ligand, the rate of formation, the yield, and the number of isomeric forms of the resulting radiopharmaceuticals, the ability to administer said ancillary or co-ligand to a patient without adverse physiological consequences to said patient, and the compatibility of the ligand in a lyophilized kit formulation. The charge and lipophilicity of the ancillary ligand will affect the charge and lipophilicity of the radiopharmaceuticals. For example, the use of 4,5-dihydroxy-1,3-benzene disulfonate results in radiopharmaceuticals with an additional two anionic groups because the sulfonate groups will be anionic under physiological conditions. The use of N-alkyl substituted 3,4-hydroxypyridinones results in radiopharmaceuticals with varying degrees of lipophilicity depending on the size of the alkyl substituents.

Preferred technetium radiopharmaceuticals of the present invention are comprised of a hydrazido or diazenido bonding unit and an ancillary ligand, $A_{L1}$, or a bonding unit and two types of ancillary $A_{L1}$ and $A_{L2}$, or a tetradentate chelator comprised of two nitrogen and two sulfur atoms. Ancillary ligands $A_{L1}$ are comprised of two or more hard donor atoms such as oxygen and amine nitrogen (sp$^3$ hybridized). The donor atoms occupy at least two of the sites in the coordination sphere of the radionuclide metal; the ancillary ligand $A_{L1}$ serves as one of the three ligands in the ternary ligand system. Examples of ancillary ligands $A_{L1}$ include but are not limited to dioxygen ligands and functionalized. aminocarboxylates. A large number of such ligands are available from commercial sources.

Ancillary dioxygen ligands include ligands that coordinate to the metal ion through at least two oxygen donor atoms. Examples include but are not limited to: glucoheptonate, gluconate, 2-hydroxyisobutyrate, lactate, tartrate, mannitol, glucarate, maltol, Kojic acid, 2,2-bis (hydroxymethyl)propionic acid, 4,5-dihydroxy-1,3-benzene disulfonate, or substituted or unsubstituted 1,2 or 3,4 hydroxypyridinones. (The names for the ligands in these examples refer to either the protonated or non-protonated forms of the ligands.)

Functionalized aminocarboxylates include ligands that have a combination of amine nitrogen and oxygen donor atoms. Examples include but are not limited to: iminodiacetic acid, 2,3-diaminopropionic acid, nitrilotriacetic acid, N,N'-ethylenediamine diacetic acid, N,N,N'-ethylenediamine triacetic acid, hydroxyethylethylenediamine triacetic acid, and N,N'-ethylenediamine bishydroxyphenylglycine. (The names for the ligands in these examples refer to either the protonated or non-protonated forms of the ligands.)

A series of functionalized aminocarboxylates are disclosed by Bridger et. al. in U.S. Pat. No. 5,350,837, herein incorporated by reference, that result in improved rates of formation of technetium labeled hydrazino modified proteins. We have determined that certain of these aminocarboxylates result in improved yields of the radiopharmaceuticals of the present invention. The preferred ancillary ligands $A_{L1}$ functionalized aminocarboxylates that are derivatives of glycine; the most preferred is tricine (tris (hydroxymethyl)methylglycine).

The most preferred technetium radiopharmaceuticals of the present invention are comprised of a hydrazido or diazenido bonding unit and two types of ancillary designated $A_{L1}$ and $A_{L2}$, or a diaminedithiol chelator. The second type of ancillary ligands $A_{L2}$ are comprised of one or more soft donor atoms selected from the group: phosphine phosphorus, arsine arsenic, imine nitrogen (sp$^2$ hybridized), sulfur (sp$^2$ hybridized) and carbon (sp hybridized); atoms which have p-acid character Ligands $A_{L2}$ can be monodentate, bidentate or tridentate, the denticity is defined by the number of donor atoms in the ligand. One of the two donor atoms in a bidentate ligand and one of the three donor atoms in a tridentate ligand must be a soft donor atom. We have disclosed in co-pending U.S. Ser. No. 08/415,908, and U.S. Ser. Nos. 60/013360 08/646,886, the disclosures of which are herein incorporated by reference in their entirety, that radiopharmaceuticals comprised of one or more ancillary or co-ligands $A_{L2}$ are more stable compared to radiopharmaceuticals that are not comprised of one or more ancillary ligands, $A_{L2}$; that is, they have a minimal number of isomeric forms, the relative ratios of which do not change significantly with time, and that remain substantially intact upon dilution.

The ligands $A_{L2}$ that are comprised of phosphine or arsine donor atoms are trisubstituted phosphines, trisubstituted arsines, tetrasubstituted diphosphines and tetrasubstituted diarsines. The ligands $A_{L2}$ that are comprised of imine nitrogen are unsaturated or aromatic nitrogen-containing, 5 or 6-membered heterocycles. The ligands that are comprised of sulfur (sp$^2$ hybridized) donor atoms are thiocarbonyls, comprised of the moiety C=S. The ligands comprised of carbon (sp hybridized) donor atoms are isonitriles, comprised of the moiety CNR, where R is an organic radical. A large number of such ligands are available from commercial sources. Isonitriles can be synthesized as described in European Patent 0107734 and in U.S. Pat. No. 4,988,827, herein incorporated by reference.

Preferred ancillary ligands $A_{L2}$ are trisubstituted phosphines and unsaturated or aromatic 5 or 6 membered heterocycles. The most preferred ancillary ligands $A_{L2}$ are trisubstituted phosphines and unsaturated 5 membered heterocycles.

The ancillary ligands $A_{L2}$ may be substituted with alkyl, aryl, alkoxy, heterocycle, aralkyl, alkaryl and arylalkaryl groups and may or may not bear functional groups comprised of heteroatoms such as oxygen, nitrogen, phosphorus or sulfur. Examples of such functional groups include but are not limited to: hydroxyl, carboxyl, carboxamide, nitro, ether, ketone, amino, ammonium, sulfonate, sulfonamide, phosphonate, and phosphonamide. The functional groups may be chosen to alter the lipophilicity and water solubility of the ligands that may affect the biological properties of the radiopharmaceuticals, such as altering the distribution into non-target tissues, cells or fluids, and the mechanism and rate of elimination from the body.

Chelators or bonding moieties for therapeutic radiopharmaceuticals are selected to form stable complexes with the radioisotopes that have alpha particle, beta particle, Auger or Coster-Kronig electron emissions, such as $^{186}Re$, $^{188}Re$, $^{153}Sm$, $^{166}Ho$, $^{177}Lu$, $^{149}Pm$, $^{90}Y$, $^{212}Bi$, $^{103}Pd$, $^{109}Pd$, $^{159}Gd$, $^{140}La$, $^{198}Au$, $^{199}Au$, $^{169}Yb$, $^{175}Yb$, $^{165}Dy$, $^{166}Dy$, $^{67}Cu$, $^{105}Rh$, $^{111}Ag$, and $^{192}Ir$. Chelators for rhenium, copper, palladium, platinum, iridium, rhodium, silver and gold isotopes are selected from diaminedithiols, monoamine-monoamidedithiols, triamide-monothiols, monoamine-diamide-monothiols, diaminedioximes, and hydrazines. Chelators for yttrium, bismuth, and the lanthanide isotopes are selected from cyclic and acyclic polyaminocarboxylates such as DTPA, DOTA, DO3A, 2-benzyl-DOTA, alpha-(2-phenethyl)1,4,7,10-tetraazacyclododecane-1-acetic-4,7,10-tris(methylacetic)acid, 2-benzyl-cyclohexyldiethylenetriaminepentaacetic acid, 2-benzyl-6-methyl-DTPA, and 6,6"-bis(N,N,N",N"-tetra(carboxymethyl)aminomethyl)-4'-(3-amino-4-methoxyphenyl)-2,2':6',2"-terpyridine.

Chelators for magnetic resonance imaging contrast agents are selected to form stable complexes with paramagnetic metal ions, such as Gd(III), Dy(III), Fe(III), and Mn(II), are selected from cyclic and acyclic polyaminocarboxylates such as DTPA, DOTA, DO3A, 2-benzyl-DOTA, alpha-(2-phenethyl)1,4,7,10-tetraazacyclododecane-1-acetic-4,7,10-tris(methylacetic)acid, 2-benzyl-cyclohexyldiethylenetriaminepentaacetic acid, 2-benzyl-6-methyl-DTPA, and 6,6"-bis[N,N,N",N"-tetra(carboxymethyl)aminomethyl)-4"-(3-amino-4-methoxyphenyl)-2,2':6',2"-terpyridine.

The technetium and rhenium radiopharmaceuticals of the present invention comprised of a hydrazido or diazenido bonding unit can be easily prepared by admixing a salt of a radionuclide, a reagent of the present invention, an ancillary ligand $A_{L1}$, an ancillary ligand $A_{L2}$, and a reducing agent, in an aqueous solution at temperatures from 0 to 100° C. The technetium and rhenium radiopharmaceuticals of the present invention comprised of a tetradentate chelator having two nitrogen and two sulfur atoms can be easily prepared by admixing a salt of a radionuclide, a reagent of the present invention, and a reducing agent, in an aqueous solution at temperatures from 0 to 100° C.

When the bonding unit in the reagent of the present invention is present as a hydrazone group, then it must first be converted to a hydrazine, which may or may not be protonated, prior to complexation with the metal radionuclide. The conversion of the hydrazone group to the hydrazine can occur either prior to reaction with the radionuclide, in which case the radionuclide and the ancillary or co-ligand or ligands are combined not with the reagent but with a hydrolyzed form of the reagent bearing the chelator or bonding unit, or in the presence of the radionuclide in which case the reagent itself is combined with the radionuclide and the ancillary or co-ligand or ligands. In the latter case, the pH of the reaction mixture. must be neutral or acidic.

Alternatively, the radiopharmaceuticals of the present invention comprised of a hydrazido or diazenido bonding unit can be prepared by first admixing a salt of a radionuclide, an ancillary ligand $A_{L1}$, and a reducing agent in an aqueous solution at temperatures from 0 to 100° C. to form an intermediate radionuclide complex with the ancillary ligand $A_{L1}$ then adding a reagent of the present invention and an ancillary ligand $A_{L2}$ and reacting further at temperatures from 0 to 100° C.

Alternatively, the radiopharmaceuticals of the present invention comprised of a hydrazido or diazenido bonding unit can be prepared by first admixing a salt of a radionuclide, an ancillary ligand $A_{L1}$, a reagent of the present invention, and a reducing agent in an aqueous solution at temperatures from 0 to 100° C. to form an intermediate radionuclide complex, and then adding an ancillary ligand $A_{L2}$ and reacting further at temperatures from 0 to 100° C.

The technetium and rhenium radionuclides are preferably in the chemical form of pertechnetate or perrhenate and a pharmaceutically acceptable cation. The pertechnetate salt form is preferably sodium pertechnetate such as obtained from commercial Tc-99m generators. The amount of pertechnetate used to prepare the radiopharmaceuticals of the present invention can range from 0.1 mCi to 1 Ci, or more preferably from 1 to 200 mCi.

The amount of the reagent of the present invention used to prepare the technetium and rhenium radiopharmaceuticals of the present invention can range from 0.01 pg to 10 mg, or more preferably from 0.5 $\mu$g to 200 $\mu$g. The amount used will be dictated by the amounts of the other reactants and the identity of the radiopharmaceuticals of the present invention to be prepared.

The amounts of the ancillary ligands $A_{L1}$ used can range from 0.1 mg to 1 g, or more preferably from 1 mg to 100 mg. The exact amount for a particular radiopharmaceutical is a function of identity of the radiopharmaceuticals of the present invention to be prepared, the procedure used and the amounts and identities of the other reactants. Too large an amount of $A_{L1}$ will result in the formation of by-products comprised of technetium labeled $A_{L1}$ without a biologically active molecule or by-products comprised of technetium labeled biologically active molecules with the ancillary ligand $A_{L1}$ but without the ancillary ligand $A_{L2}$. Too small an amount of $A_{L1}$ will result in other by-products such as technetium labeled biologically active molecules with the ancillary ligand $A_{L2}$ but without the ancillary ligand $A_{L1}$, or reduced hydrolyzed technetium, or technetium colloid.

The amounts of the ancillary ligands $A_{L2}$ used can range from 0.001 mg to 1 g, or more preferably from 0.01 mg to 10 mg. The exact amount for a particular radiopharmaceutical is a function of the identity of the radiopharmaceuticals of the present invention to be prepared, the procedure used and the amounts and identities of the other reactants. Too large an amount of $A_{L2}$ will result in the formation of by-products comprised of technetium labeled $A_{L2}$ without a biologically active molecule or by-products comprised of technetium labeled biologically active molecules with the ancillary ligand $A_{L2}$ but without the ancillary ligand $A_{L1}$. If the reagent bears one or more substituents that are comprised of a soft donor atom, as defined above, at least a ten-fold molar excess of the ancillary ligand $A_{L2}$ to the reagent of formula 2 is required to prevent the substituent from interfering with the coordination of the ancillary ligand $A_{L2}$ to the metal radionuclide.

Suitable reducing agents for the synthesis of the radiopharmaceuticals of the present invention include stannous salts, dithionite or bisulfite salts, borohydride salts, and formamidinesulfinic acid, wherein the salts are of any pharmaceutically acceptable form. The preferred reducing agent is a stannous salt. The amount of a reducing agent used can range from 0.001 mg to 10 mg, or more preferably from 0.005 mg to 1 mg.

The specific structure of a radiopharmaceutical of the present invention comprised of a hydrazido or diazenido bonding unit will depend on the identity of the reagent of the present invention used, the identity of any ancillary ligand $A_{L1}$, the identity of any ancillary ligand $A_{L2}$, and the identity of the radionuclide. Radiopharmaceuticals comprised of a hydrazido or diazenido bonding unit synthesized using concentrations of reagents of <100 $\mu$g/mL, will be comprised of one hydrazido or diazenido group. Those synthesized using >1 mg/mL concentrations will be comprised of two hydrazido or diazenido groups from two reagent molecules. For most applications, only a limited amount of the biologically active molecule can be injected and not result in undesired side-effects, such as chemical toxicity, interference with a biological process or an altered biodistribution of the radiopharmaceutical. Therefore, the radiopharmaceuticals that require higher concentrations of the reagents comprised in part of the biologically active molecule, will have to be diluted or purified after synthesis to avoid such side-effects.

The identities and amounts used of the ancillary ligands $A_{L1}$ and $A_{L2}$ will determine the values of the variables y and z. The values of y and z can independently be an integer from 1 to 2. In combination, the values of y and z will result in a technetium coordination sphere that is made up of at least five and no more than seven donor atoms. For monodentate ancillary ligands $A_{L2}$, z can be an integer from 1 to 2; for bidentate or tridentate ancillary ligands $A_{L2}$, z is 1. The preferred combination for monodentate ligands is y equal to 1 or 2 and z equal to 1. The preferred combination for bidentate or tridentate ligands is y equal to 1 and z equal to 1.

The indium, copper, gallium, silver, palladium, rhodium, gold, platinum; bismuth, yttrium and lanthanide radiopharmaceuticals of the present invention can be easily prepared by admixing a salt of a radionuclide and a reagent of the present invention, in an aqueous solution at temperatures from 0 to 100° C. These radionuclides are typically obtained as a dilute aqueous solution in a mineral acid, such as hydrochloric, nitric or sulfuric acid. The radionuclides are combined with from one to about one thousand equivalents of the reagents of the present invention dissolved in aqueous solution. A buffer is typically used to maintain the pH of the reaction mixture between 3 and 10.

The gadolinium, dysprosium, iron and manganese metallopharmaceuticals of the present invention can be easily prepared by admixing a salt of the paramagnetic metal ion and a reagent of the present invention, in an aqueous solution at temperatures from 0 to 100° C. These paramagnetic metal ions are typically obtained as a dilute aqueous solution in a mineral acid, such as hydrochloric, nitric or sulfuric acid. The paramagnetic metal ions are combined with from one to about one thousand equivalents of the reagents of the present invention dissolved in aqueous solution. A buffer is typically used to maintain the pH of the reaction mixture between 3 and 10.

The total time of preparation will vary depending on the identity of the metal ion, the identities and amounts of the reactants and the procedure used for the preparation. The preparations may be complete, resulting in >80% yield of the radiopharmaceutical, in 1 minute or may require more time. If higher purity metallopharmaceuticals are needed or desired, the products can be purified by any of a number of techniques well known to those skilled in the art such as liquid chromatography, solid phase extraction, solvent extraction, dialysis or ultrafiltration.

Buffers useful in the preparation of metallopharmaceuticals and in diagnostic kits useful for the preparation of said radiopharmaceuticals include but are not limited to phosphate, citrate, sulfosalicylate, and acetate. A more complete list can be found in the United States. Pharmacopeia.

Lyophilization aids useful in the preparation of diagnostic kits useful for the preparation of radiopharmaceuticals include but are not limited to mannitol, lactose, sorbitol, dextran, Ficoll, and polyvinylpyrrolidine (PVP).

Stabilization aids useful in the preparation of metallopharmaceuticals and in diagnostic kits useful for the preparation of radiopharmaceuticals include but are not limited to ascorbic acid, cysteine, monothioglycerol, sodium bisulfite, sodium metabisulfite, gentisic acid, and inositol.

Solubilization aids useful in the preparation of metallopharmaceuticals and in diagnostic kits useful for the preparation of radiopharmaceuticals include but are not limited to ethanol, glycerin, polyethylene glycol, propylene glycol, polyoxyethylene sorbitan monooleate, sorbitan monoloeate, polysorbates, poly(oxyethylene)poly(oxypropylene)poly (oxyethylene) block copolymers (Pluronics) and lecithin. Preferred solubilizing aids are polyethylene glycol, and Pluronics.

Bacteriostats useful in the preparation of metallopharmaceuticals and in diagnostic kits useful for the preparation of radiopharmaceuticals include but are not limited to benzyl alcohol, benzalkonium chloride, chlorbutanol, and methyl, propyl or butyl paraben.

A component in a diagnostic kit can also serve more than one function. A reducing agent can also serve as a stabilization aid, a buffer can also serve as a transfer ligand, a lyophilization aid can also serve as a transfer, ancillary or co-ligand and so forth.

The diagnostic radiopharmaceuticals are administered by intravenous injection, usually in saline solution, at a dose of 1 to 100 mCi per 70 kg body weight, or preferably at a dose of 5 to 50 mCi. Imaging is performed using known procedures.

The therapeutic radiopharmaceuticals are administered by intravenous injection, usually in saline solution, at a cl dose of 0.1 to 100 mCi per 70 kg body weight, or preferably at a dose of 0.5 to 5 mCi per 70 kg body weight.

The magnetic resonance imaging contrast agents of the present invention may be used in a similar manner as other MRI agents as described in U.S. Pat. Nos. 5,155,215; 5,087,440; Margerstadt et al., Magn. Reson. Med., 1986, 3, 808; Runge et al., Radiology, 1988, 166, 835; and Bousquet et al., Radiology, 1988, 166, 693. Generally, sterile aqueous solutions of the contrast agents are administered to a patient intravenously in dosages ranging. from 0.01 to 1.0 mmoles per kg body weight.

For use as X-ray contrast agents, the compositions of the present invention should generally have a heavy atom concentration of 1 mM to 5 M, preferably 0.1 M to 2 M. Dosages, administered by intravenous injection, will typically range from 0.5 mmol/kg to 1.5 mmol/kg, preferably 0.8 mmol/kg to 1.2 mmol/kg. Imaging is performed using known techniques, preferably X-ray computed tomography.

The ultrasound contrast agents of the present invention are administered by intravenous injection in an amount of 10 to 30 µL of the echogenic gas per kg body weight or by infusion at a rate of approximately 3 µL/kg/min. Imaging is performed using known techniques of sonography.

Other features of the invention will become apparent in the course of the following descriptions of exemplary embodiments that are given for illustration of the invention and are not intended to be limiting thereof.

EXAMPLES

Representative materials and methods that may be used in preparing the compounds of the invention are described further below. All chemicals and solvents (reagent grade) were used as supplied from the vendors cited without further purification. Fmoc-amino acids and other starting amino acids may be obtained commercially from Bachem Inc., Bachem Biosciences Inc. (Philadelphia, Pa.), Advanced ChemTech (Louisville, Ky.), Peninsula Laboratories (Belmont, Calif.), Novabiochem (Calif.), RSP Amino Acid Analogues (Worcester, Mass.) or Sigma (St. Louis, Mo.). 2-(1H-Benzotriazol-1-yl)-1,1,3,3-tetramethyluronium hexafluorophosphate (HBTU) and TBTU were purchased from Advanced ChemTech. N-methylmorpholine (NMM), m-cresol, D-2-aminobutyric acid (Abu), diisopropylethylamine (DIEA), 1,2,4-triazole, stannous chloride dihydrate, and tris(3-sulfonatophenyl)phosphine trisodium salt (TPPTS) were purchased from Aldrich Chemical Company. Bis(3-sulfonatophenyl)phenylphosphine disodium salt (TPPDS) was prepared by the published procedure (Kuntz, E., U.S. Pat. No. 4,248,802). (3-Sulfonatophenyl) diphenylphosphine monosodium salt (TPPMS)was purchased from TCI America, Inc. Tricine was obtained from Research Organics, Inc. Technetium-99m-pertechnetate ($^{99m}TcO_4^-$) was obtained from a DuPont Pharma $^{99}Mo/^{99m}Tc$ Technelite® generator. In-111-chloride (Indichlor®) was obtained from Amersham Medi-Physics, Inc. Sm-153-chloride was obtained from the University of Missouri Research Reactor (MURR). Dimethylformamide (DMF), ethyl acetate, chloroform ($CHCl_3$), methanol (MeOH), pyridine and hydrochloric acid (HCl) were obtained from Baker. Acetonitrile, dichloromethane (DCM), acetic acid (HOAc), trifluoroacetic acid (TFA), ethyl ether, triethylamine, acetone, and magnesium sulfate were commercially obtained. Absolute ethanol was obtained from Quantum Chemical Corporation.

General Procedure for Solid Phase Peptide Synthesis (SPPS) Using Fmoc—Chemistry on the-HMPB-BHA Resin for the Preparation of Cyclic Peptides The appropriately protected linear peptide precursors to the cyclic peptides, described in the Examples, were prepared by automated solid phase peptide synthesis using Fmoc chemistry on an Advanced ChemTech Model ACT90 Synthesizer and using HMPB-BHA resin as the solid support. Synthesis of the protected pentapeptide-resin intermediates was achieved by coupling (for 3 h) the Fmoc-amino acids sequentially to the commercially available (Novabiochem) Fmoc-Gly-HMPB-BHA resin (usually 2 g, substitution 0.47 to 0.60 mmol/g) in a 50 mL reactor. Three to five equivalents each of the amino acid, diisopropylethylamine (DIPEA), HOBt and HBTU in DMF was used. The Fmoc-group was deprotected using 20% piperidine in DMF (30 min). The peptides were cleaved from the HMPB-BHA resin using a solution of 1% TFA/DCM and collecting the peptide solutions in a solution of pyridine in methanol (1:10). The linear protected peptides were isolated by removing the solvents and reagents in vacuo, followed by triturating the crude residue in diethyl ether.

The analytical HPLC methods generally utilized are described below:

| Analytical HPLC Method 1 | |
|---|---|
| Instrument: | HP1050 |
| Column: | Vydac C18 (4.6 × 250 mm) |
| Detector: | Diode array detector 220 nm/500 ref |
| Flow Rate: | 1.0 mL/min. |
| Column Temp: | 50° C. |
| Sample Size: | 15 uL |
| Mobile Phase: | A: 0.1% TFA in water |
| | B: 0.1% TFA in ACN/Water (9:1) |

| Gradient A: | Time (min) | % A | % B |
|---|---|---|---|
| | 0 | 80 | 20 |
| | 20 | 0 | 100 |
| | 30 | 0 | 100 |
| | 31 | 80 | 20 |

| Analytical HPLC Method 2 | |
|---|---|
| Instrument: | HP1050 |
| Column: | Vydac C18 (4.6 × 250 mm) |
| Detector: | Diode array detector 220 nm/500 ref |
| Flow Rate: | 1.0 mL/min. |
| Column Temp: | 50° C. |
| Sample Size: | 15 uL |
| Mobile Phase: | A: 0.1% TFA in water |
| | B: 0.1% TFA in ACN/Water (9:1) |

| Gradient B: | Time (min) | % A | %B |
|---|---|---|---|
| | 0 | 98 | 2 |
| | 16 | 63.2 | 36.8 |
| | 18 | 0 | 100 |
| | 28 | 0 | 100 |
| | 30 | 98 | 2 |

Example 1

Synthesis of 2-[7-(4-{(4S)-4-[N-(4-{(4S,10S,13S,1R)-4-[2-(2-amino(3,4,5,6-tetrahydropyrimidin-4-yl))ethyl]-3,6,9,12,15-pentaaza-10-(carboxymethyl)-2,5,8,11,14-pentaoxo-13-benzylcyclopentadecyl}butyl)carbamoyl]-4-[(6-{[(1Z)-1-aza-2-(2-sulfophenyl)vinyl]amino}(3-pyridyl))carbonylamino]-butanoylamino}butyl)(1S,4S,7S,10S)-10-[2-(2-amino(3,4,5,6-tetrahydropyrimidin-4-yl))ethyl]-3,6,9,12,15-pentaaza-2,5,8,11,14-pentaoxo-4-benzylcyclopentadecyl]acetic acid

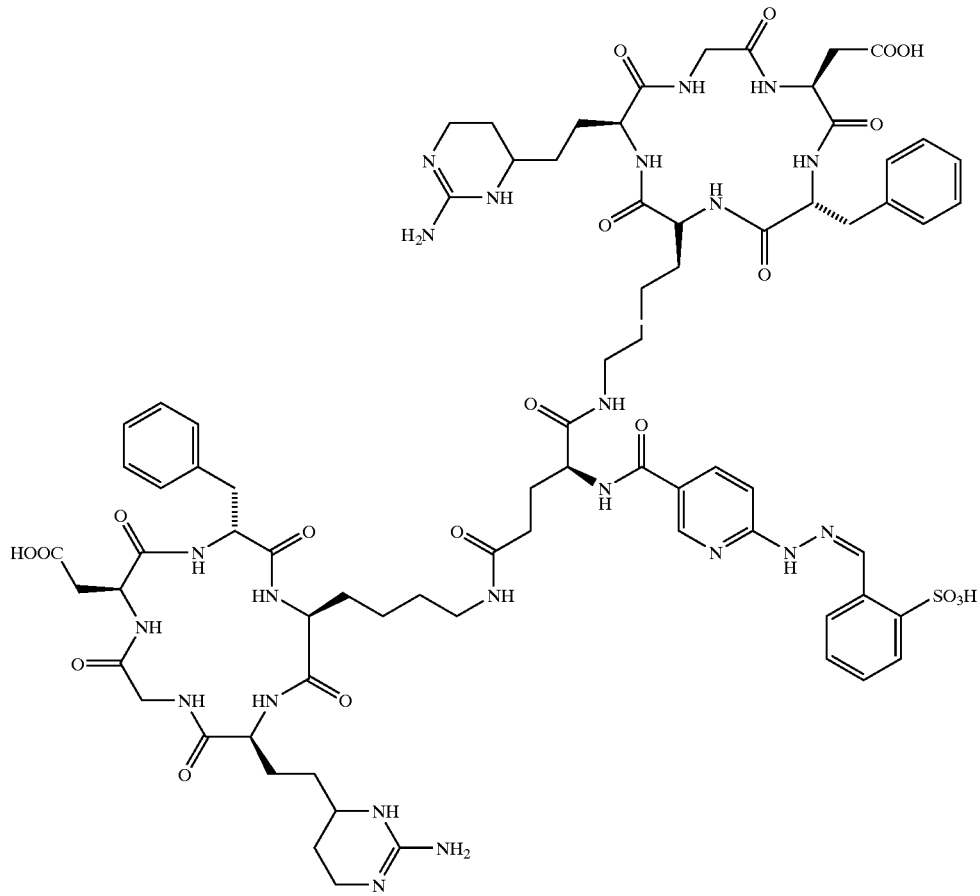

Part A

Preparation of tert-butyl 2-((1S,4S,10S,7R)-10-[2-(2-aminopyrimidin-4-yl)ethyl]-3,6,9,12,15-pentaaza-7-{4-[(tert-butoxy)carbonylamino]butyl}-2,5,8,11,14-pentaoxo-4-benzylcyclopentadecyl)acetate

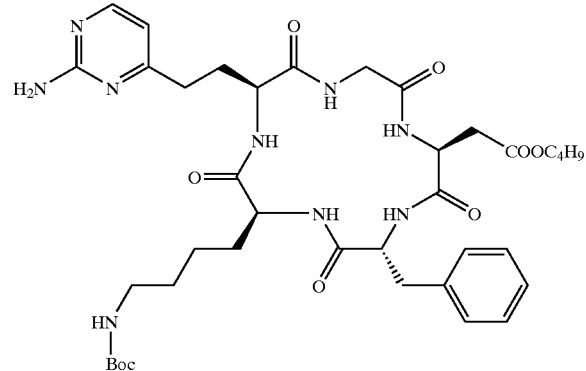

To a stirred solution of HBTU (0.43 g, 1.13 mmol) in 8 mL DMF maintained at 60° C. under nitrogen for 5 min. was added, dropwise, a solution of 2-{2-[(2R)-2-((2S)-2-{(2S)-2-amino-3-[(tert-butyl)oxycarbonyl]propanoylamino}-3-phenyl-propanoylamino)-6-[(tert-butoxy)carbonylamino]-hexanoylamino](2S)-4-(2-aminopyrimidin-4-yl)butanoylamino}-acetic acid (0.65 g, 0.71 mmol), prepared via SPPS as described above, and diisopropylethylamine (0.40 mL, 2.3 mmol) in DMF (8 mL). The solution was maintained at 60° C. for 5 h, cooled, the solvent was removed in vacuo, and the oil was triturated in ethyl acetate (50 mL). The solid product thus obtained was filtered, washed with ethyl acetate, and dried in vacuo to give 0.38 g of the desired product as a dark tan solid. ESMS [M+H]$^{+1}$: 782.5; calc. 782.4. Analytical HPLC indicated the product to be adequately pure for the next step.

Part B

Preparation of 2-{(1S,4S,10S,7R)-10-[2-(2-amino(3,4,5,6-tetrahydropyrimidin-4-yl))ethyl]-7-(4-aminobutyl)-3,6,9,12,15-pentaaza-2,5,8,11,14-pentaoxo-4-benzylcyclopentadecyl}acetic acid

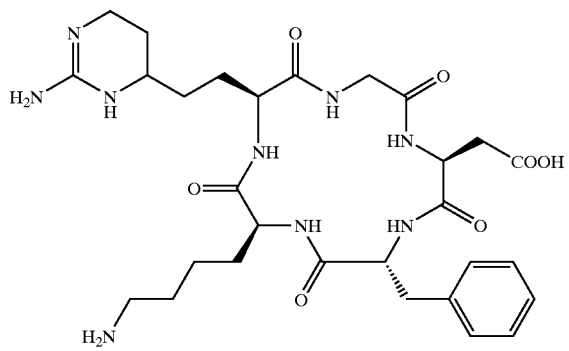

The crude peptide tert-butyl 2-((1S,4S,10S,7R)-10-[2-(2-aminopyrimidin-4-yl)ethyl]-3,6,9,12,15-pentaaza-7-{4-[(tert-butoxy)carbonylamino]butyl}-2,5,8,11,14-pentaoxo-4-benzylcyclopentadecyl)acetate(0.35 g) was added to a mixture of TFA (2.9 mL), TIPS (75 μL) and water (75 μL) and the reaction mixture was stirred overnight at room temperature under nitrogen. The volatiles were removed in vacuo and the crude solid (370 mg) isolated via trituration in diethyl ether (60 mL). Since the reaction was incomplete, the crude (340 mg) was redissolved in TFA (2.5 mL) and TIPS (0.5 mL) and stirred at room temperature under nitrogen for about 48 h. The volatiles were removed in vacuo and the residue triturated in diethyl ether to give the desired compound (0.3 g). The crude material was purified by reversed phase preparative HPLC to give 180 mg of the product. HRMS: Calculated for $C_{29}H_{44}N_9O_7$, 630.3364; found 630.3380

Part C

Preparation of 2-[7-(4-{(4S)-4-[N-(4-{(4S,10S,13S,1R)-4-[2-(2-amino(3,4,5,6-tetrahydropyrimidin-4-yl))ethyl]-3,6,9,12,15-pentaaza-10-(carboxymethyl)-2,5,8,11,14-pentaoxo-13-benzylcyclopentadecyl}butyl)carbamoyl]-4-[(tert-butoxy)carbonylamino]-butanoylamino}butyl)(1S,4S,7S,10S)-10-[2-(2-amino(3,4,5,6-tetrahydropyrimidin-4-yl))ethyl]-3,6,9,12,15-pentaaza-2,5,8,11,14-pentaoxo-4-benzylcyclopentadecyl]acetic acid

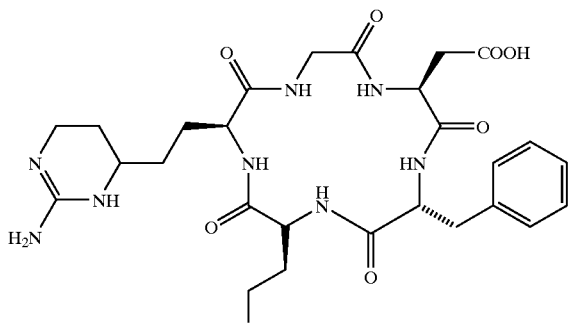

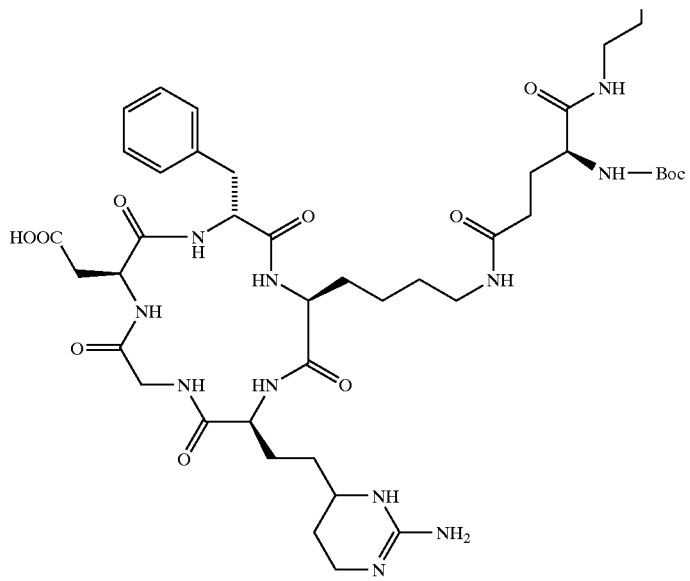

To a solution of 2-{(1S,4S,10S,7R)-10-[2-(2-amino(3,4,5,6-tetrahydropyrimidin-4-yl))ethyl]-7-(4-aminobutyl)-3,6,9,12,15-pentaaza-2,5,8,11,14-pentaoxo-4-benzylcyclopentadecyl}acetic acid (100 mg, 117 mmol) in DMF (8 mL) at room temperature under nitrogen was added triethylamine (100 μh, 6 eq.). The reaction mixture was stirred for 5 min. and Boc-Glu(OTFP)-OTFP (ARH7971-115, 32 mg, 58 mmol) added in four portions over 90 min. The solution was stirred overnight, the solvent removed in vacuo, and the residue was triturated in ethyl acetate, filtered using additional ethyl acetate to transfer material and dried in vacuo to give 81 mg of the desired product. ESMS [M+H]$^{+1}$: 1470.6; calc. 1470.7.

Part D

Preparation of 2-[7-(4-{(4S)-4-[N-(4-{(4S,10S,13S,1R)-4-[2-(2-amino(3,4,5,6-tetrahydropyrimidin-4-yl))ethyl]-3,6,9,12,15-pentaaza-10-(carboxymethyl)-2,5,8,11,14-pentaoxo-13-benzylcyclopentadecyl}butyl)carbamoyl]-4-aminobutanoylamino}butyl)(1S,4S,7S,10S)-10-[2-(2-amino(3,4,5,6-tetrahydropyrimidin-4-yl))ethyl]-3,6,9,12,15-pentaaza-2,5,8,11,14-pentaoxo-4-benzylcyclopentadecyl]acetic acid. Tris TFA salt A solution of 2-[7-(4-{(4S)-4-[N-(4-{(4S,10S,13S,1R)-4-[2-(2-amino(3,4,5,6-tetrahydropyrimidin-4-yl))ethyl]-3,6,9,12,15-pentaaza-10-(carboxymethyl)-2,5,8,11,14-pentaoxo-13-benzylcyclopentadecyl}butyl)carbamoyl]-4-[(tert-butoxy)carbonylamino]butanoylamino}butyl)(1S,4S,7S,10S)-10-[2-(2-amino(3,4,5,6-tetrahydropyrimidin-4-yl))ethyl]-3,6,9,12,15-pentaaza-2,5,8,11,14-pentaoxo-4-benzylcyclopentadecyl]acetic acid (72.5 mg) was dissolved in 50:50 TFA:DCM and stirred for 3 h at room temperature under nitrogen. The volatiles were removed in vacuo and the crude residue triturated in diethyl ether, filtered, washed with diethyl ether (2×5 mL), and dried in vacuo to give the crude product as an off-white solid (66 mg). ESMS [M+H]$^{+1}$: 1370.5; calc. 1370.7. The crude product was purified by reversed phase preparative HPLC to give 26 mg of the purified product, as the tris TFA salt. HRMS: Calculated for $C_{63}H_{92}N_{19}O_{16}$,1370.6969; found 1370.698.

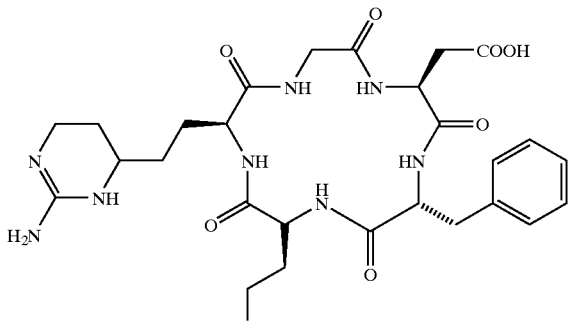

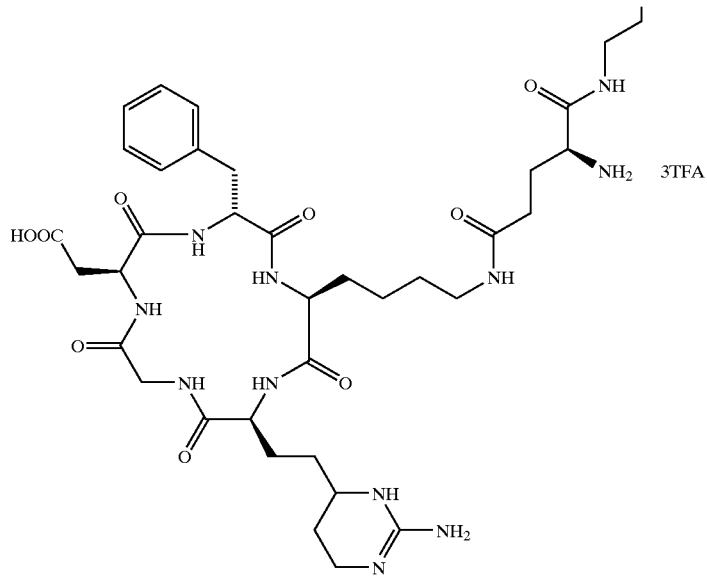

Part E

Preparation of 2-[7-(4-{(4S)-4-[N-(4-{(4S,10S,13S,1R)-4-[2-(2-amino(3,4,5,6-tetrahydropyrimidin-4-yl))ethyl]-3,6,9,12,15-pentaaza-10-(carboxymethyl)-2,5,8,11,14-pentaoxo-13-benzylcyclopentadecyl}butyl)carbamoyl]-4-[(6-{[(1Z)-1-aza-2-(2-sulfophenyl)vinyl]-amino}(3-pyridyl))carbonylamino]-butanoylamino}butyl)-(1S,4S,7S,10S)-10-[2-(2-amino(3,4,5,6-tetrahydropyrimidin-4-yl))ethyl]-3,6,9,12,15-pentaaza-2,5,8,11,14-pentaoxo-4-benzylcyclopentadecyl]acetic acid To a solution of 2-[7-(4-{(4S)-4-[N-(4-{(4S,10S,13S,1R)-4-[2-(2-amino(3,4,5,6-tetrahydropyrimidin-4-yl))ethyl]-3,6,9,12,15-pentaaza-10-(carboxymethyl)-2,5,8,11,14-pentaoxo-13-benzylcyclopentadecyl}-butyl)carbamoyl]-4-aminobutanoylamino}butyl)(1S,4S,7S,10S)-10-[2-(2-amino(3,4,5,6-tetrahydropyrimidin-4-yl))ethyl]-3,6,9,12,15-pentaaza-2,5,8,11,14-pentaoxo-4-benzylcyclopentadecyl]acetic acid (15.5 mg) in DMF (200 µL) was added triethylamine (7 µL). After 5 min of stirring 2-[[[5-[[(2,5-dioxo-1-pyrrolidinyl)oxy]carbonyl]-2-pyridinyl]hydrazono]methyl]-benzenesulfonic acid, monosodium salt (5.7 mg) was added. The reaction mixture was stirred overnight (~18 h) and then concentrated under high vacuum. The residue was triturated in ethyl acetate to give the desired crude product (23.6 mg). LCMS: Calcd. for $C_{76}H_{100}N_{22}O_{20}S$, 1672.7; Found, 1674.4 $[M+H]^{+1}$.

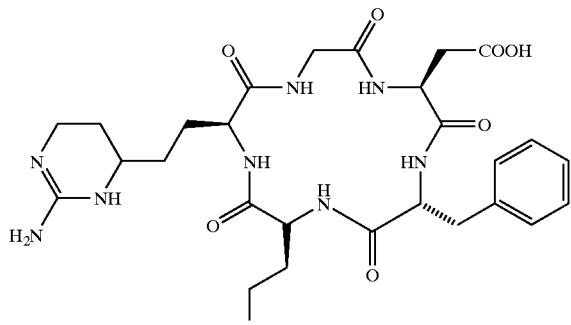

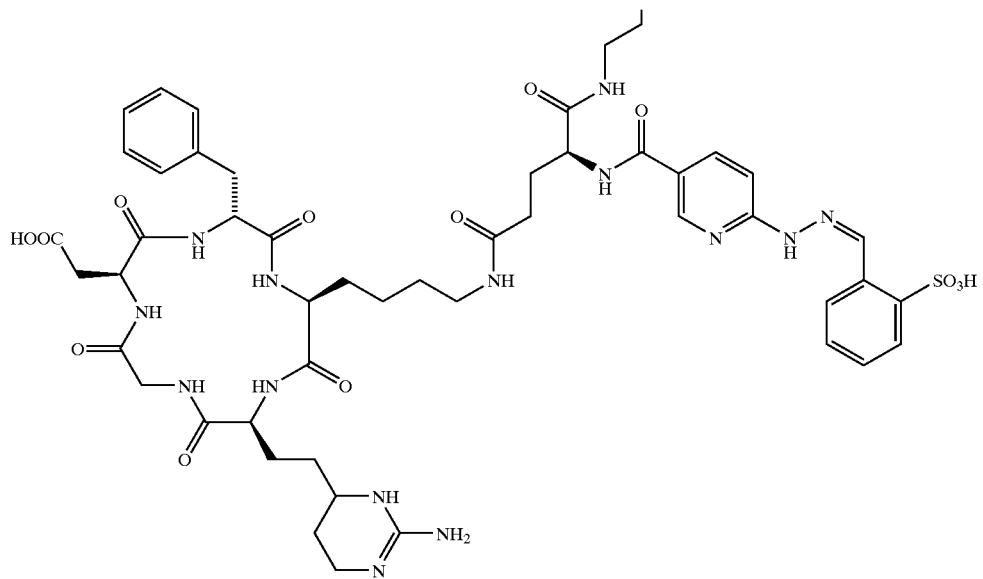

Example 2

Synthesis of 2-((1S,4S,10S,7R)-7-{4-[(6-{[(1Z)-1-aza-2-(2-sulfophenyl)vinyl]amino}(3-pyridyl))carbonylamino]butyl}-10-[2-(2-amino(3,4,5,6-tetrahydropyrimidin-4-yl))ethyl]-3,6,9,12,15-pentaaza-2,5,8,11,14-pentaoxo-4-benzylcyclopentadecyl)acetic acid To a solution of 2-{(1S,4S,10S,7R)-10-[2-(2-amino(3,4,5,6-tetrahydropyrimidin-4-yl))ethyl]-7-(4-aminobutyl)-3,6,9,12,15-pentaaza-2,5,8,11,14-pentaoxo-4-benzylcyclopentadecyl}acetic acid (21.5 mg) in DMF (500 µL) was added triethylamine (17.4 µL). After 5 min of stirring 2-[[[5-[[(2,5-dioxo-1-pyrrolidinyl)oxy]carbonyl]-2-pyridinyl]hydrazono]methyl]-benzenesulfonic acid, monosodium salt (14.3 mg) was added. The reaction mixture was stirred overnight (~18 h) and then concentrated under high vacuum. The residue was triturated in ethyl acetate to give the desired crude product (36.5 mg). LCMS: Calcd. for $C_{42}H_{52}N_{12}O_{11}S$, 932.4; Found, 933.3 $[M+H]^{+1}$.

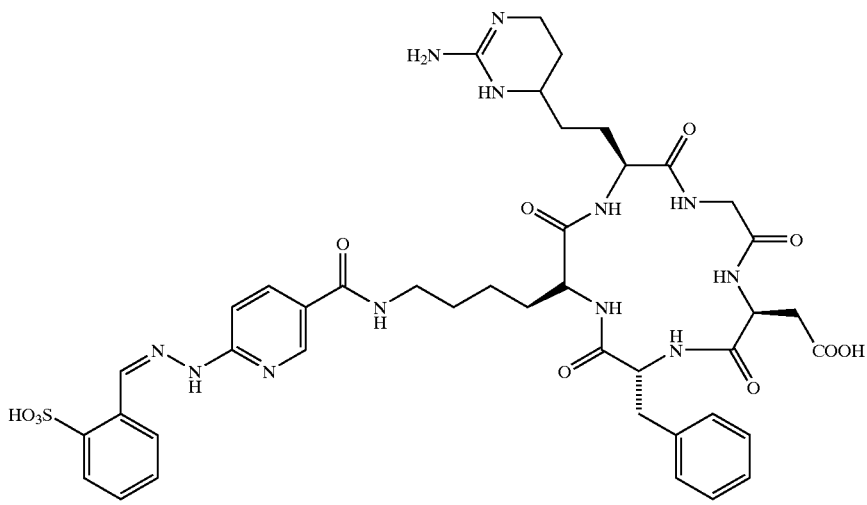

Example 3

Synthesis of 2-[(1S,4S,10S,7R)-10-[2-(2-amino(3,4,5,6-tetrahydropyrimidin-4-yl))ethyl]-3,6,9,12,15-pentaaza-2,5,8,11,14-pentaoxo-4-benzyl-7-(4-{2-[1,4,7,10-tetraaza-4,7,10-tris(carboxymethyl)cyclododecyl]acetylamino}-butyl)cyclopentadecyl]acetic acid

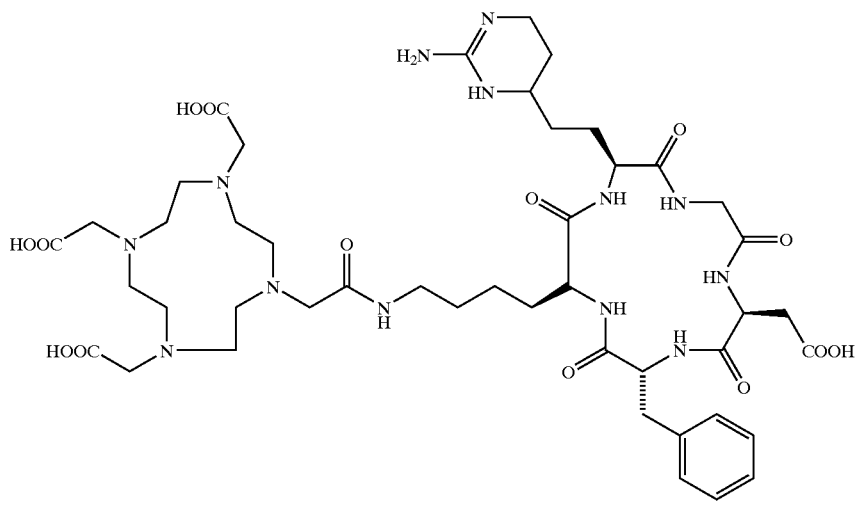

A solution of the commercially (Macrocyclics) available DOTA tri-t-butyl ester (1.5 mmol) and Hunig's base (6 mmol) in anhydrous DMF are treated with HBTU (1.25 mmol) and allowed to react for 15 min at ambient temperatures under nitrogen. 2-{(1S,4S,10S,7R)-10-[2-(2-Amino(3,4,5,6-tetrahydropyrimidin-4-yl))ethyl]-7-(4-aminobutyl)-3,6,9,12,15-pentaaza-2,5,8,11,14-pentaoxo-4-benzylcyclopentadecyl}acetic acid, bis TFA salt (1 mmol) is added to this solution and stirring is continued at ambient temperatures under nitrogen for 18 h. The DMF is removed under vacuum and the resulting residue is triturated in ethyl acetate or diethyl ether and filtered. If necessary, the crude is purified by preparative HPLC on a C18 column using a water:ACN:0.1% TFA gradient and the product fraction is lyophilized to give the DOTA-conjugate. The DOTA conjugate is stirred in degassed TFA at room temperature under nitrogen for 2 h. The solution is concentrated and the resulting residue is purified by preparative HPLC on a C18 column using a water:ACN:0.1% TFA gradient. The product fraction is lyophilized to give the title compound.

Example 4

Synthesis of 2-[7-(4-{(4S)-4-[N-(4-{(4S,10S,13S,1R)-4-[2-(2-amino(3,4,5,6-tetrahydropyrimidin-4-yl))ethyl]-3,6,9,12,15-pentaaza-10-(carboxymethyl)-2,5,8,11,14-pentaoxo-13-benzylcyclopentadecyl}butyl)carbamoyl]-4-{2-[1,4,7,10-tetraaza-4,7,10-tris(carboxymethyl)cyclododecyl]-acetylamino}butanoylamino}butyl)(1S,4S,7S,10S)-10-[2-(2-amino(3,4,5,6-tetrahydropyrimidin-4-yl))ethyl]-3,6,9,12,15-pentaaza-2,5,8,11,14-pentaoxo-4-benzylcyclopentadecyl]acetic acid

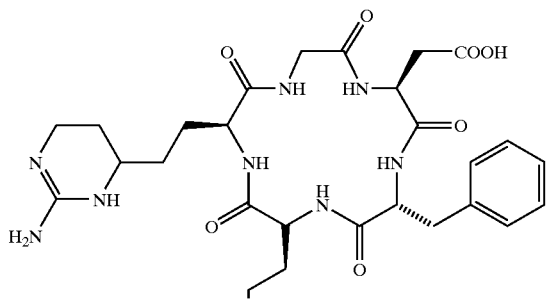

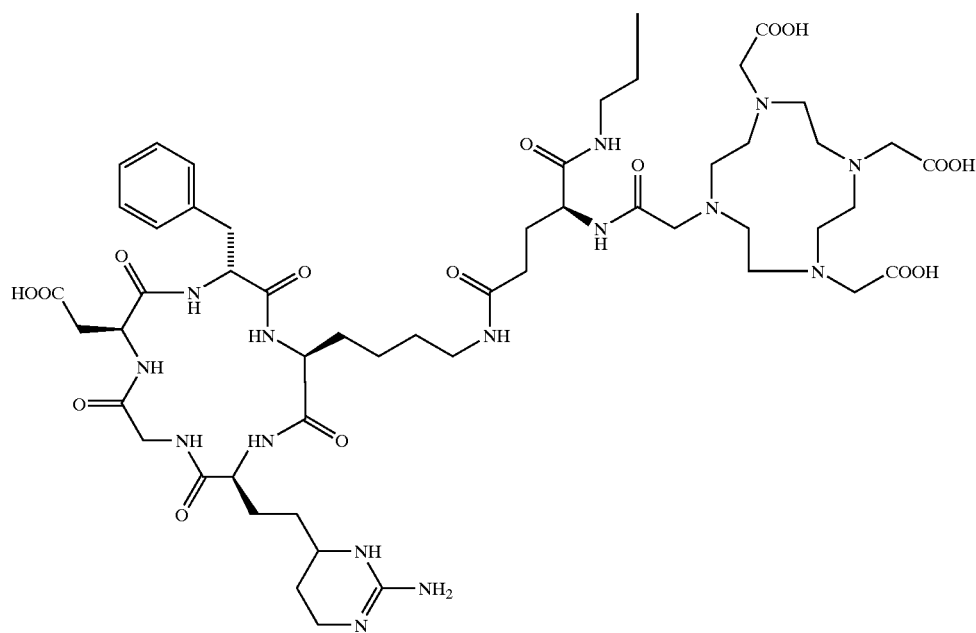

A solution of the commercially (Macrocyclics) available DOTA tri-t-butyl ester (1.5 mmol) and Hunig's base (6 mmol) in anhydrous DMF are treated with HBTU (1.25 mmol) and allowed to react for 15 min at ambient temperatures under nitrogen. 2-[7-(4-{(4S)-4-[N-(4-{(4S,10S,13S,1R)-4-[2-(2-Amino(3,4,5,6-tetrahydropyrimidin-4-yl))ethyl]-3,6,9,12,15-pentaaza-10-(carboxymethyl)-2,5,8,11,14-pentaoxo-13-benzylcyclopentadecyl}-butyl)carbamoyl]-4-aminobutanoylamino}butyl)(1S,4S,7S,10S)-10-[2-(2-amino(3,4,5,6-tetrahydropyrimidin-4-yl))ethyl]-3,6,9,12,15-pentaaza-2,5,8,11,14-pentaoxo-4-benzylcyclopentadecyl]acetic acid, tris TFA salt (1 mmol) is added to this solution and stirring is continued at ambient temperatures under nitrogen for 18 h. The DMF is removed under vacuum and the resulting residue is triturated in ethyl acetate or diethyl ether and filtered. If necessary, the crude is purified by preparative HPLC on a C18 column using a water:ACN:0.1% TFA gradient and the product fraction is lyophilized to give-the DOTA-conjugate. The DOTA conjugate is stirred in degassed TFA at room temperature under nitrogen for 2 h. The solution is concentrated and the resulting residue is purified by preparative HPLC on a C18 column using a water:ACN:0.1% TFA gradient. The product fraction is lyophilized to give the title compound.

UTILITY

The diagnostic radiopharmaceuticals are administered by intravenous injection, usually in saline solution, at a dose of 1 to 100 mCi per 70 kg body weight, or preferably at a dose of 5 to 50 mCi. Imaging is performed using known procedures.

The therapeutic radiopharmaceuticals are administered by intravenous injection, usually in saline solution, at a dose of 0.1 to 100 mCi per 70 kg body weight, or preferably at a dose of 0.5 to 5 mCi per 70 kg body weight.

The magnetic resonance imaging contrast agents of the present invention may be used in a similar manner as other MRI agents as described in U.S. Pat. Nos. 5,155,215; 5,087,440; Margerstadt et al., Magn. Reson. Med., 1986, 3, 808; Runge et al., Radiology, 1988, 166, 835; and Bousquet et al., Radiology, 1988, 166, 693. Generally, sterile aqueous solutions of the contrast agents are administered to a patient intravenously in dosages ranging from 0.01 to 1.0 mmol per kg body weight.

For use as X-ray contrast agents, the compositions of the present invention should generally have a heavy atom. concentration of 1 mM to 5 M, preferably 0.1 M to 2 M. Dosages, administered by intravenous injection, will typically range from 0.5 mmol/kg to 1.5 mmol/kg, preferably 0.8 mmol/kg to 1.2 mmol/kg. Imaging is performed using known techniques, preferably X-ray computed tomography.

The pharmaceuticals of the present invention are useful for imaging hypoxia, apoptosis, cardiac ischemia, thrombosis, infection, inflammation, cancer, restenosis, atherosclerosis, diabetic retinopathy, macular degeneration, wound healing, and reperfusion injury, in a patient. The imaging radiopharmaceuticals of the present invention comprised of a gamma ray or positron emitting isotope. The radiopharmaceuticals of the present invention comprised of a beta, alpha or Auger electron emitting isotope are useful for treatment of pathological processes including cancer, rstenosis, diabetic retinopathy, and macular degeneration, by delivering a cytotoxic dose of radiation to the locus of expression of the receptor or enzyme with which the BM interacts (targets). The treatment of cancer is affected by the systemic administration of the radiopharmaceuticals resulting in a cytotoxic radiation dose to tumors.

The compounds of the present invention comprised of one or more paramagnetic metal ions selected from gadolinium, dysprosium, iron, and manganese, are useful as contrast agents for magnetic resonance imaging (MRI) of hypoxia, apoptosis, cardiac ischemia, thrombosis, infection, inflammation, cancer, restenosis, atherosclerosis, diabetic, retinopathy, macular degeneration, wound healing, and reperfusion injury.

The compounds of the present invention comprised of one or more heavy atoms with atomic number of 20 or greater are useful as X-ray contrast agents for X-ray imaging of hypoxia, apoptosis, cardiac ischemia, thrombosis, infection, inflammation, cancer, restenosis, atherosclerosis, diabetic retinopathy, macular degeneration, wound healing, and reperfusion injury.

Biochemical assays and in vivo models for testing the pharmaceuticals of the present invention are described in U.S. Pat. No. 5,879,657, PCT Application WO 98/15295, and PCT Application WO 99/51628. The assays and models described are incorporated herein by reference.

Obviously, numerous modifications and variations of the present invention are possible in light of the above teachings. It is therefore to be understood that within the scope of the appended claims, the invention may be practiced otherwise that as specifically described herein.

What is claimed is:

1. A compound of formula I:

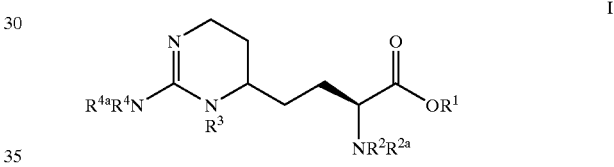

or a stereoisomer or salt form thereof, wherein:
$R^1$ is H or a carboxylic acid protecting group; alternatively, $OR^1$ is an activated ester;
$R^2$ is H, $CH_3$, or an amine protecting group;
$R^{2a}$ is H or an amine protecting group;
$R^3$ is H or an amine protecting group;
$R^4$ is H or an amine protecting group; and
$R^{4a}$ is H or an amine protecting group;
provided that one of $R^1$, $R^2$, $R^{2a}$, $R^3$, $R^4$, $R^{4a}$ is other than H.

2. A compound formula Ia or Ib:

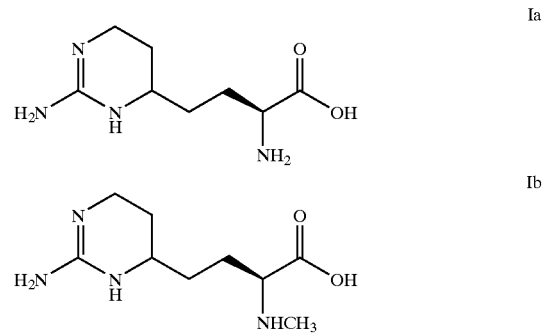

or a stereoisomer or salt form thereof.

3. A compound according to claim 1, wherein:
$R^1$ is selected from H, OMe, OEt, OBzl, Oallyl, and Ot-Bu;

alternatively, $OR^1$ is selected from OSu, OBt, OPfp, and Onp;
$R^2$ is Fmoc or Boc;
$R^{2a}$ is H;
$R^3$ is H;
$R^4$ is selected from Tos, Mtr, Pbf, Mts, Pmc, Boc, Mbs, $NO_2$, and Cbz; and
$R^{4a}$ is H;
alternatively, when $R^4$ is Boc, $R^{4a}$ is Boc; and,
alternatively, when $R^4$ is Cbz, $R^{4a}$ is Cbz.

4. A process for making a compound of formula I, comprising:

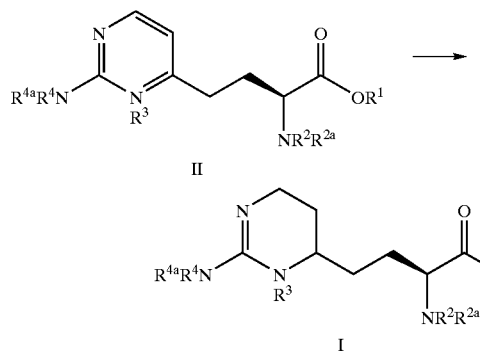

reducing a pyrimidine of formula II wherein:

$R^1$ is H or a carboxylic acid protecting group;
alternatively, $OR^1$ is an activated ester;
$R^2$ is H, $CH_3$, or an amine protecting group;
$R^{2a}$ is H or an amine protecting group;
$R^3$ is H or an amine protecting group;
$R^4$ is H or an amine protecting group; and
$R^{4a}$ is H or an amine protecting group;
provided that one of $R^1$, $R^2$, $R^{2a}$, $R^3$, $R^4$, $R^{4a}$ is other than H.

5. A process according to claim 4, wherein reduction is performed by contacting the compound of formula II with trifluoroacetic acid and a trialkylsilane.

6. A process according to claim 5, wherein the trialkylsilane is triisopropylsilane.

7. A method of preparing an arginine-containing peptide, comprising: synthesizing the peptide using a compound of formula I in place of arginine or protected arginine:

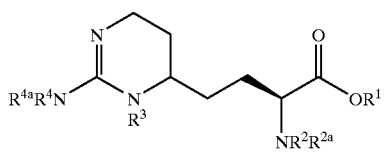

or a stereoisomer or salt form thereof, wherein:
$R^1$ is H or a carboxylic acid protecting group;
alternatively, $OR^1$ is an activated ester;
$R^2$ is H or an amine protecting group;
$R^{2a}$ is H or an amine protecting group;
$R^3$ is H or an amine protecting group;
$R^4$ is H or an amine protecting group; and
$R^{4a}$ is H or an amine protecting group;
provided that one of $R^1$, $R^2$, $R^{2a}$, $R^3$, $R^4$, $R^{4a}$ is other than H.

8. A compound, comprising: an acyclic or cyclic peptide that targets a biological receptor, wherein the peptide comprises an arginine mimic of formula IIIa or IIIb:

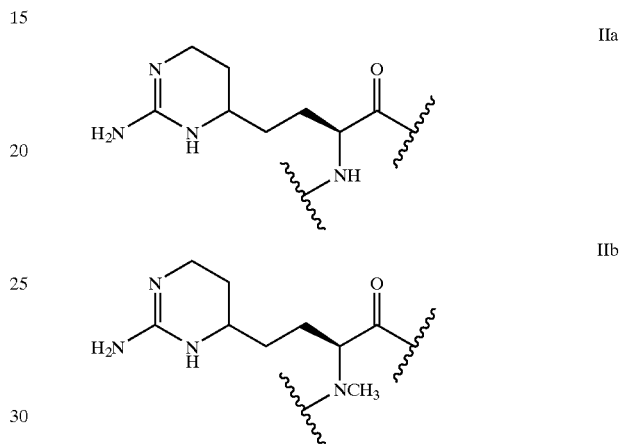

wherein ⌇ represents a bond to the remainder of the peptide or the C-terminus or N-terminus of the peptide.

9. A compound according to claim 8, wherein the biological receptor is selected from the group: Tuftsin, Thrombin catalytic site, Thrombin exosite, Factor XIIIa, Factor Xa, Factor IXa, Factor VIIa, Neurotensin, Bombesin, the Bradykinin receptors, and an intergrin selected from $a_vb_3$, $a_{IIb}b_3$, $a_vb_5$, $a_5b_1$, $a_2b_1$, $a_1b_1$, and Mac-1.

10. A compound according to claim 8, wherein the biological receptor is selected from the group: Tuftsin, Thrombin catalytic site, Thrombin exosite, Factor XIIIa, Factor Xa, Factor IXa, Factor VIIa, and an intergrin selected from $a_vb_3$, $a_{IIb}b_3$, $a_vb_5$, $a_5b_1$, $a_2b_1$, $a_1b_1$, and Mac-1.

11. A compound according to claim 9, wherein the compound comprises an RGD, TKPR, or TKPPR segment wherein the arginine or arginine-mimetic has been replaced by the arginine mimic of formula IIIa or IIIb.

12. A compound according to claim 9, wherein the compound further comprises: a chelator and 0–1 linking groups between the peptide and the chelator.

13. A compound according to claim 11, wherein the linking group is present.

14. A compound according to claim 3, wherein $R^4$ is Boc and $R^{4a}$ is Boc.

15. A compound according to claim 3, wherein $R^4$ is Cbz and $R^{4a}$ is Cbz.

* * * * *